US009215068B2

(12) United States Patent (10) Patent No.: US 9,215,068 B2
Iwamura et al. (45) Date of Patent: Dec. 15, 2015

(54) SEARCH SYSTEM, SEARCH METHOD, AND PROGRAM

(75) Inventors: Kana Iwamura, Tokyo (JP); Takatsugu Hirokawa, Tokyo (JP); Koji Tsuda, Tokyo (JP); Hiromi Arai, Kanagawa (JP); Jun Sakuma, Ibaraki (JP); Kiyoshi Asai, Tokyo (JP); Michiaki Hamada, Tokyo (JP); Goichiro Hanaoka, Ibaraki (JP); Koji Nuida, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 29 days.

(21) Appl. No.: 14/344,453

(22) PCT Filed: Sep. 14, 2012

(86) PCT No.: PCT/JP2012/005885
§ 371 (c)(1),
(2), (4) Date: Mar. 12, 2014

(87) PCT Pub. No.: WO2013/038698
PCT Pub. Date: Mar. 21, 2013

(65) Prior Publication Data
US 2014/0355756 A1 Dec. 4, 2014

(30) Foreign Application Priority Data
Sep. 14, 2011 (JP) ................................. 2011-200826

(51) Int. Cl.
*H04L 29/06* (2006.01)
*H04L 9/30* (2006.01)
(Continued)

(52) U.S. Cl.
CPC .............. *H04L 9/3066* (2013.01); *G06F 19/28* (2013.01); *H04L 9/008* (2013.01); *H04L 9/0861* (2013.01); *H04L 9/3046* (2013.01)

(58) Field of Classification Search
CPC ......... H04L 9/3066; H04L 9/008; H04L 9/28; H04L 2209/16; H04L 9/309
USPC ............................................................ 380/30
IPC ............................. H04L 9/3066, 9/008, 9/3093
See application file for complete search history.

(56) References Cited

U.S. PATENT DOCUMENTS 8,515,058 B1 * 8/2013 Gentry ........................... 380/28
2008/0294909 A1 * 11/2008 Ostrovsky et al. ............ 713/189
(Continued)

FOREIGN PATENT DOCUMENTS

JP 2010 164835 7/2010
JP 2011 13672 1/2011

OTHER PUBLICATIONS

C. Gentry, "Fully homomorphic encryption using ideal lattices," STOC '09: Proceedings of the 41st annual ACM symposium on Theory of computing, May 2009.*
(Continued)

*Primary Examiner* — Syed Zaidi
(74) *Attorney, Agent, or Firm* — Oblon, McClelland, Maier & Neustadt, L.L.P.

(57) ABSTRACT

A search system has a management device that stores compound data and a searcher device. The management device defines a similarity between query sequence data q representing a substructure or property of a substance that is input as a search condition at the searcher device and sequence data $p_i$ (i=1, 2, ..., m) for substances stored in the database by means of a score T that takes a non-negative value when a Tversky index $S_i$ is greater than or equal to a threshold value $\theta_n/\theta_d$ (where $\theta_n$ and $\theta_d$ are natural numbers that satisfy $\theta_n \leq \theta_d$), calculates an encrypted value of the score T while the query sequence q is maintained in an encrypted state, and returns the encrypted value to the searcher device to thereby disclose information regarding whether or not similar compounds are present in the database while in a confidential state.

13 Claims, 19 Drawing Sheets

(51) Int. Cl.
*H04L 9/00* (2006.01)
*G06F 19/28* (2011.01)
*H04L 9/08* (2006.01)

(56) References Cited

U.S. PATENT DOCUMENTS

2010/0329448 A1   12/2010  Rane et al.
2011/0110525 A1    5/2011  Gentry
2011/0264920 A1*  10/2011  Rieffel et al. .............. 713/189
2013/0170640 A1*   7/2013  Gentry ........................ 380/30

OTHER PUBLICATIONS

Shuguo Han; Wee Keong Ng; Yu, P.S., "Privacy-Preserving Singular Value Decomposition," Data Engineering, 2009. ICDE '09. IEEE 25th International Conference on, vol., No., pp. 1267,1270, Mar. 29, 2009-Apr. 2, 2009.*

Brenner, M.; Wiebelitz, J.; von Voigt, G.; Smith, M., "Secret program execution in the cloud applying homomorphic encryption," Digital Ecosystems and Technologies Conference (DEST), 2011 Proceedings of the 5th IEEE International Conference on, vol., No., pp. 114,119, May 31, 2011-Jun. 3, 2011.*

Wright, R. et al., "Privacy-Preserving Bayesian Network Structure Computation on Distributed Heterogeneous Data", Research Track Poster, Proceedings of the 10th ACM SIGKDD International Conference on Knowledge Discovery and Data Mining, pp. 713-718, (Aug. 2004).

Goethals, B. et al., "On Private Scalar Product Computation for Privacy-Preserving Data Mining", Lecture Notes in Computer Science, vol. 3506, pp. 104-120, (2005).

Singh, M. D. et al., "A Privacy Preserving Jaccard Similarity Function for Mining Encrypted Data", TENCON 2009, 2009 IEEE Region 10 Conference, Total 6 Pages, (Nov. 23-26, 2009).

International Search Report Issued Dec. 4, 2012 in PCT/JP12/005885 Filed Sep. 14, 2012.

* cited by examiner

FIG.1
COMPOUND 1
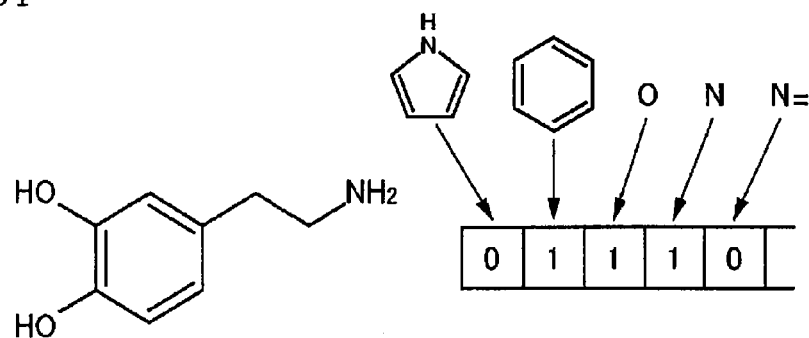
COMPOUND 2
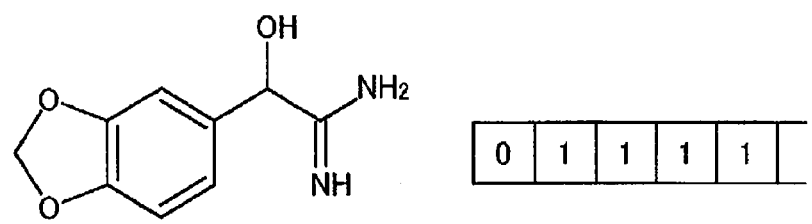
COMPOUND 3
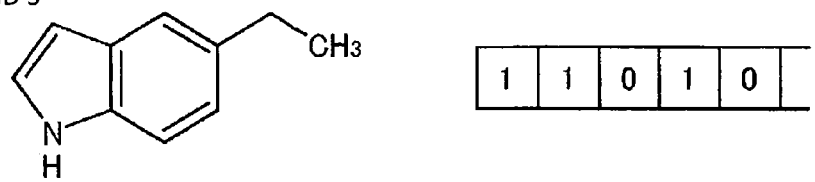

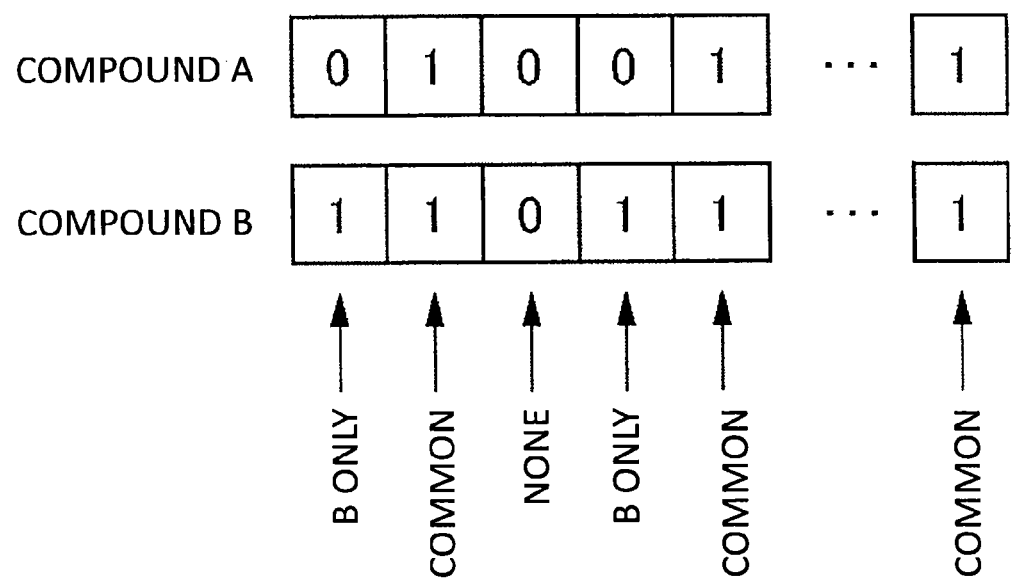

$$S = \frac{c}{\alpha(a-c) + \beta(b-c) + c}$$

SET OF PARTIAL STRUCTURES
POSSESSED BY COMPOUND A

SET OF PARTIAL STRUCTURES
POSSESSED BY COMPOUND B

FIG.3A $$\mathrm{Enc}(A+B) = \mathrm{Enc}(A) \oplus \mathrm{Enc}(B)$$

FIG.3B $$\mathrm{Enc}(A+B) = \mathrm{Enc}(A) \times \mathrm{Enc}(B)$$

FIG.3C $$\mathrm{Enc}(A \times B)$$

$$= \mathrm{Enc}(\underbrace{A + A + \cdots + A}_{\text{ADDED UP B TIMES}})$$

$$= \underbrace{\mathrm{Enc}(A) \times \mathrm{Enc}(A) \times \cdots \times \mathrm{Enc}(A)}_{\text{MULTIPLIED B TIMES}}$$

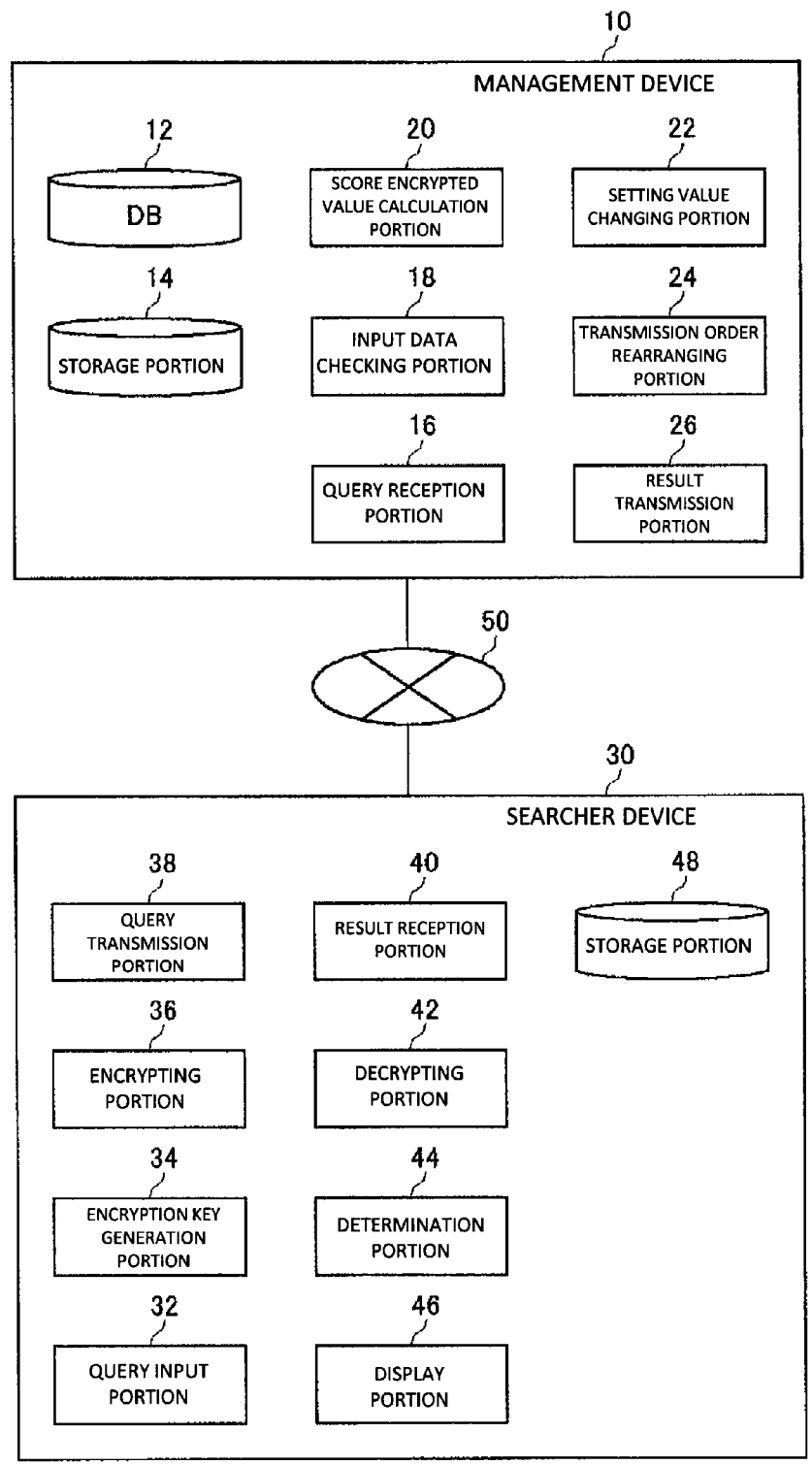

$$q = \{q_1, q_2, \cdots q_i, \cdots q_n\}$$

ENCRYPTION $$Enc(q) = \{Enc(q_1), Enc(q_2), \cdots Enc(q_i), \cdots Enc(q_n)\}$$

$Enc(p \cap q) = Enc(q_2) \times Enc(q_3) \times \cdots \times Enc(q_n)$

SEARCH SYSTEM, SEARCH METHOD, AND PROGRAM

TECHNICAL FIELD

The present invention relates to a search system and a search method for examining whether similar data is present within a database while maintaining the confidentiality of a search condition and the database.

BACKGROUND ART

Nowadays, drug discovery proceeds through the stages of a searching for a target, searching for hit compounds, searching for a lead compound, and synthesis of drug candidates to a drug development process of preclinical trials. In the search for a target, a causative gene (protein or the like) of an illness is identified by sequence information analysis (database research) or analysis of gene expression information with microarrays or the like. In the search for hit compounds, docking and MD (simulation) on a computer are performed to narrow down candidates, and structures and functions are predicted based on similar proteins, in order to search for compounds that presumably act on the causative gene. In the search for a lead compound, a search is performed for compounds that are similar to the hit compounds to find a lead compound that is more effective. When synthesizing drug candidates, verification experiments are performed with respect to compounds in the vicinity of the lead compound.

In searching for a lead compound, it is necessary to search in a database of known compounds for a compound that is similar to a hit compound. The owners of databases of known compound include public institutions such as the National Center for Biotechnology Information (NCBI) and supplier enterprises that synthesize and sell compounds.

In current drug discovery, a researcher does not want to disclose data of a hit compound that the researcher discovered to outside sources. This tendency is particularly noticeable in business enterprises. When performing a search in a public compound database, a researcher downloads all the data onto the computer of the researcher's company. However, since a search space for organic compounds has a size of 10 to the power of 60, the data amount will possibly increase in the future and it will be difficult to download and hold all the data. Further, when a researcher wants to search for compounds in the compound database of a business enterprise, a researcher purchases the data after entering a confidentiality agreement with the enterprise. However, because it is not possible for the researcher to know in advance whether or not the purchased database includes compounds that are similar to a hit compound, the purchase of the database may unfortunately be a wasted investment.

On the other hand, enterprises that provide compound databases adopt a selling model in which the enterprises make databases that have a low level of confidentiality publicly available for free, and sell a so-called "focused library" that has a high level of confidentiality. A focused library is a database that is a collection of useful compounds that the enterprise spends resources on to prepare, and in which it is expected that hits are especially liable to occur. Generally, a focused library accumulates compounds which are considered to be highly effective with respect to a specific drug discovery target (for example, GPCR or kinase or the like). However, if the enterprise does not disclose any of the information in a focused library, researchers that are concerned with wasteful investment will have a negative attitude with regard to purchasing the data, and the enterprise will risk losing business opportunities.

Therefore, if a researcher can know whether or not compounds similar to a compound that the researcher has in hand is present in a database while the researcher keeps the compound that the researcher has discovered secret as well as the database provider keeps the contents of the database secret, this will be advantageous to both the researcher and the database provider.

Heretofore, almost no research has been conducted with regard to methods for determining the similarity of respective compounds while maintaining confidentiality. As far as the present inventors are aware, the only prior research performed in this respect is disclosed in Non Patent Literature 1 that relates to securely calculating the similarity (Tanimoto coefficient) of respective compounds. According to the method proposed in Non Patent Literature 1, a process is repeated in which a researcher and a database owner respectively encrypt elements of a vector that represents a compound and send the encrypted elements to a third party, and the third party determines whether the respective elements from the researcher and the database owner match, and the process is repeated.

CITATION LIST

Non Patent Literature

Non Patent Literature 1: M. D. Singh et al., "A privacy preserving Jaccard similarity function for mining encrypted data", IEEE TENCON 2009

SUMMARY OF INVENTION

Technical Problem

However, the method described in Non Patent Literature 1 involves a third party who may be allowed to see confidential information, in addition to the researcher that has a hit compound to be used for a search condition and the owner of the database. Further, since communication occurs as many as elements of a vector, the method is less practicable.

The present invention, which has been made in view of the above background, provides a search system and a search method that make it possible to examine whether or not a database includes data that is similar to a search condition in a state in which the respective information of the owner of the database and the user of the database is kept secret from each other.

Solution to Problem

A search system of the present invention comprises a management device having a database that stores data representing a substructure or a property of a substance, and a searcher device for inputting a search condition and outputting a search result of the database. Here, the data is sequence data in which, with respect to a predetermined plurality of substructures or properties, "1" is set in a case where a substance has the substructure or property, and "0" is set in a case where the substance does not have the substructure or property. The search system executes the following steps to examine whether the database includes sequence data $p_i$ (i=1, 2, ..., m; m represents a number of sequence data items) for which a Tversky index $S_i$ $$S_i = \frac{|p_i \cap q|}{\frac{\mu_a}{\gamma}(|q| - |p_i \cap q|) + \frac{\mu_b}{\gamma}(|p_i| - |p_i \cap q|) + |p_i \cap q|}$$ [Equation 1]

where $\mu_a$, $\mu_b$, and $\gamma$ represent 0 or natural numbers that satisfy $$0 \leq \frac{\mu_a}{\gamma}, 0 \leq \frac{\mu_b}{\gamma}$$

$|p_i|$ represents a number of elements having a value of "1" that are included in sequence data $p_i$ $|q|$ represents a number of elements having a value of "1" that are included in sequence data q $(|p_i \cap q|)$ represents a number of elements having a value of "1" that are included in both of sequence data $p_i$ and sequence data q is greater than or equal to a threshold value $\theta_n/\theta_d$ (where $\theta_n$ and $\theta_d$ are natural numbers which satisfy $\theta_n \leq \theta_d$) with respect to query sequence data q that represents a substructure or a property of a substance that is input as a search condition at the searcher device and the sequence data $p_i$ of a substance stored in the database.

(1) The searcher device generates a public key and a private key of a cryptosystem having an additive homomorphic property.

(2) The searcher device accepts input of query sequence data q.

(3) The searcher device determines a number of elements $|q|$ having a value of "1" among elements constituting the query sequence data q, encrypts a value obtained by attaching a minus sign to the number of elements $|q|$ with the public key, and encrypts a value of each element $q_j$ (where j=1, ..., n; n represents a length of the query sequence q) of the query sequence data q with the public key.

(4) The searcher device outputs the public key, the encrypted value Enc(-|q|), and encrypted values Enc($q_1$), Enc($q_2$), ..., Enc($q_n$) of each element of the query sequence data q to the management device.

(5) The management device receives the public key, the encrypted value Enc(-|q|) and the encrypted values Enc($q_1$), Enc($q_2$), ..., Enc($q_n$) of each element of the query sequence data q that are output from the searcher device.

(6) The management device reads out one item of sequence data $p_i$ from the database.

(7) The management device determines a number of elements $|p_i|$ having a value of "1" among elements constituting the sequence data $p_i$, and encrypts a value obtained by attaching a minus sign to the number of elements $|p_i|$ with the public key.

(8) The management device examines each element $p_{i,j}$ (where j=0, 1, ... n; n represents a length of sequence data $p_i$) of the sequence data $p_i$, utilizes the additive homomorphic property of the cryptosystem to perform on an encrypted value Enc($q_k$) a calculation corresponding to addition in plaintext of all elements $q_k$ (k satisfies $p_{i,k}$=1) of the query sequence data q that correspond to elements having a value of "1" in the sequence data $p_i$, and determines an encrypted value Enc($|p_i \cap q|$) of a number of elements $|p_i \cap q|$ having a value of "1" in both of the query sequence data q and the sequence data $p_i$.

(9) The management device utilizes the additive homomorphic property of the cryptosystem to perform a calculation corresponding to a calculation in which $(|p_i \cap q|)$ is added up $\gamma(\theta_d - \theta_n) + \theta_n(\mu_a + \mu_b)$ times in plaintext on the encrypted value Enc($|p_i \cap q|$), and determines an encrypted value Enc($(|p_i \cap q|) \times \{\gamma(\theta_d - \theta_n) + \theta_n(\mu_a + \mu_b)\}$).

(10) The management device utilizes the additive homomorphic property of the cryptosystem to perform a calculation corresponding to a calculation in which (-|q|) is added up $\mu_a$ times in plaintext on the encrypted value Enc(-|q|) to determine an encrypted value Enc($\mu_a(-|q|)$), performs a calculation corresponding to a calculation in which (-|$p_i$|) is added up $\mu_b$ times in plaintext on the encrypted value Enc(-|$p_i$|) to determine an encrypted value Enc($\mu_b(-|p_i|)$), performs a calculation corresponding to $\mu_a(-|q|)+\mu_b(-|p_i|)$ in plaintext on the encrypted value Enc($\mu_a(-|q|)$) and the encrypted value Enc($\mu_b(-|p_i|)$) to determine an encrypted value Enc($\mu_a(-|q|)+\mu_b(-|p_i|)$), and further performs a calculation corresponding to a calculation in which $\mu_a(-|q|)+\mu_b(-|p_i|)$ is added up $\theta_n$ times in plaintext on the encrypted value Enc($\mu_a(-|q|)+\mu_b(-|p_i|)$) to determine an encrypted value Enc($\theta_n(\mu_a(-|q|)+\mu_b(-|p_i|))$).

(11) The management device utilizes the additive homomorphic property of the cryptosystem to perform a calculation corresponding to $(|p_i \cap q|) \times \{\gamma(\theta_d - \theta_n) + \theta_n(\mu_a + \mu_b)\} + \theta_n(\mu_a(-|q|)+\mu_b(-|p_i|))$ in plaintext on the encrypted value Enc($(|p_i \cap q|) \times \{\gamma(\theta_d - \theta_n) + \theta_n(\mu_a + \mu_b)\}$) determined in the above (9) and the encrypted value Enc($\theta_n(\mu_a(-|q|)+\mu_b(-|p_i|))$) determined in the above (10), and determines an encrypted value Enc($(|p_i \cap q|) \times \{\gamma(\theta_d - \theta_n) + \theta_n(\mu_a + \mu_b)\} + \theta_n(\mu_a(-|q|)+\mu_b(-|p_i|))$) as an encrypted value of a score $T_i$.

(12) The management device repeats the above (6) to (11) for each of a plurality of items of sequence data $p_i$ included in the database, and determines an encrypted value of the score $T_i$ for each of the items of sequence data $p_i$.

(13) The management device outputs the encrypted values of the scores $T_1, T_2, \ldots, T_m$ to the searcher device.

(14) The searcher device receives the encrypted values of the scores $T_1, T_2, \ldots, T_m$ that are output from the management device.

(15) The searcher device decrypts the encrypted values of the scores $T_1, T_2, \ldots, T_m$ with the private key.

(16) The searcher device determines whether the scores $T_1, T_2, \ldots, T_m$ are non-negative or negative.

(17) The searcher device outputs the determination result.

In the present invention, the cryptosystem may be a probabilistic cryptosystem. Further, a calculation corresponding to addition in plaintext may be multiplication in cases of encrypted values. A Paillier cryptosystem can be used as a cryptosystem that has these properties.

In addition, apart from utilizing a cryptosystem having an additive homomorphic property that is mentioned here, it is also possible in the present invention to utilize a cryptosystem having a multiplicative homomorphic property and an additive homomorphic property.

Advantageous Effects of Invention

According to the present invention, because a management device uses a value obtained by encrypting query sequence data q to calculate a score $T_i$ for determining a Tversky index $S_i$, the confidentiality of the query sequence data q can be maintained. Further, since the score $T_i$ only shows whether or not data for a substance stored in a database has a degree of similarity that is greater than a predetermined threshold value $\theta_n/\theta_d$, the contents of the database are not directly divulged to the searcher. Thus, it is possible to obtain information showing whether or not the database includes data for substances that are similar to a query while maintaining the confidentiality of the query sequence data q and the database.

BRIEF DESCRIPTION OF DRAWINGS

FIG. 1 is a view for describing a fingerprint.

FIG. 2A is a view illustrating an example in which two fingerprints are compared.

FIG. 3A is a view for explaining an additive homomorphism.

FIG. 3B is a view for explaining an additive homomorphic property of a Paillier cryptosystem.

FIG. 3C is a view illustrating an example that calculates an encrypted value Enc(A×B) of a value A×B while in the encrypted state.

FIG. 4 is a view illustrating a configuration of a search system according to a first embodiment.

DESCRIPTION OF EMBODIMENTS

A search system and a search method according to embodiments of the present invention are described hereunder with reference to the drawings. Although in the following description a compound that is represented by a fingerprint is taken as an example of a structure, the present invention is not limited to a search for a compound, and the present invention can be applied to data in which a structure or a property of a substance can be expressed with sequence data of "1" and "0" (for example, a database in which genes are stored).

A fingerprint and a Tversky index will first be described prior to describing the configuration and operations of the search system.

(Fingerprint)

FIG. 1 is a view illustrating an example of a fingerprint. A fingerprint is a way of representing a compound. A fingerprint represents whether or not a compound has a predetermined substructure with a sequence of numbers that takes "1" and "0" as elements. In the example shown in FIG. 1, the fingerprint represents the presence or absence of a "pyrrole ring", a "benzene ring", "O", "N", and a "double bond of N" in order from the first bit. A "0" value for an element indicates that the relevant structure is not present, and a "1" value indicates that the relevant structure is present. With respect to compound 1, since "1" is set in the second to fourth bits, the compound 1 includes a "benzene ring", "O", and "N", and since the values of the first and fifth bits are "0", the compound 1 does not include a "pyrrole ring" or a "double bond of N".

Methods of representing a compound using a fingerprint in this manner include an MDL MACCS key, a Daylight fingerprint, an ECFP (extended connectivity fingerprint), a FCFP (functional class fingerprint), and a pharmacophore key. An example of an MDL MACCS key is shown in FIG. 1.

Although data for only five bits is shown as one example in FIG. 1, the length of an actual fingerprint is longer, and for example is 960 bits in the case of an MDL MACCS key. The present invention can be applied to whatever fingerprints of any kind are used.

(Tversky Index)

As shown in FIG. 2A, the number of substructures common to compounds A and B and the number of substructures included only in compound A or compound B, respectively, are found by comparing the fingerprints of compounds A and B. The similarity of compounds A and B can be assessed based on the comparison results. Note that it is not necessary to take into consideration a substructure that is not included either in the compounds A and B.

Figures 2B, 2C:
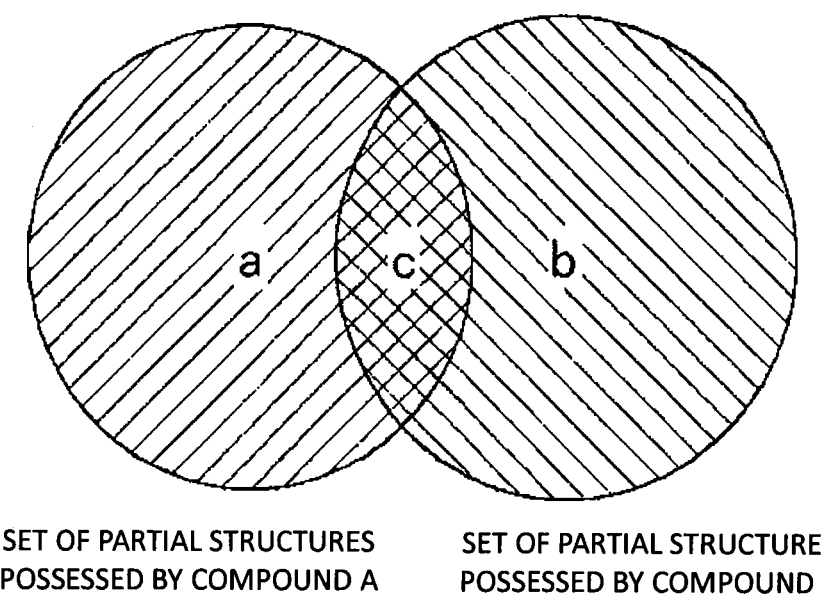
FIG. 2B is a view showing a Tversky index $S_i$.
FIG. 2C is a view for explaining the Tversky index.

FIG. 2B is a view illustrating a Tversky index S. FIG. 2C is a view for describing the Tversky index. Reference character "a" denotes a set of substructures that compound A has, and corresponds to a circle on the left side in FIG. 2C. Reference character "b" denotes a set of substructures that compound B has, and corresponds to a circle on the right side in FIG. 2C. Reference character "c" denotes a set (logical product) of substructures that compounds A and B commonly have, and corresponds to an overlapping portion of the two circles in FIG. 2C.

The symbols "α" and "β" in the Tversky index represent coefficients that take a value greater than or equal to 0. The similarity between the compounds A and B can be measured from different viewpoints by appropriately setting the coefficients α and β. When α=1 and β=1, S=c/(a+b−c). This coefficient is referred to as a "Tanimoto coefficient", and represents the proportion of common substructures among all the substructures that the compounds A and B have. When α=1 and β=0, S=c/a. This represents what proportion of the compound A is included as a substructure in the compound B. When α=½ and β=½, S=c/{(a+b)/2}, which is a value obtained by dividing the number of sets of substructures that the compounds A and B commonly have by the average of the number of substructures that the compound A has and the number of substructures that the compound B has. This is referred to as "Dice's coefficient". In each case, the greater the value that the index S is, the higher the rate of similarity between the compound A and the compound B is.

(Outline of Present Embodiment)

The search system of the present embodiment examines compounds for which a Tversky index is greater than or equal to a predetermined threshold value with respect to a fingerprint of a compound (referred to as a "query") input at a searcher device. Specifically, the system examines how many compounds that are similar to the query are present in a database. At such time, a search is performed in a management device that manages the database while keeping the query secret. To realize this, according to the search system of the present embodiment, the management device performs calculations on encrypted values as they are by using a probabilistic cryptosystem having an additive homomorphic property. An additive homomorphism will now be described.

FIG. 3A is a view for describing an additive homomorphism. Note that in the present specification, "Enc( )" represents an encrypted value in which the value inside the brackets is encrypted. An additive homomorphic cryptosystem is a cryptosystem that can perform a calculation corresponding to addition in plaintext using encrypted values. Specifically, as shown in FIG. 3A, an additive homomorphic cryptosystem has a property such that an encrypted value Enc(A) of a value A and an encrypted value Enc(B) of a value B can be computed to calculate an encrypted value Enc(A+B) of a value A+B while in the encrypted state. An operation performed on the encrypted value Enc(A) and the encrypted value Enc(B) differs depending on the kind of cryptosystem.

FIG. 3B is a view for describing an additive homomorphic property of a Paillier cryptosystem. According to the Paillier cryptosystem, as shown in FIG. 3B, the encrypted value Enc(A+B) obtained by encrypting the value A+B can be determined by multiplying the encrypted value Enc(A) by the encrypted value Enc(B). Specifically, multiplication of encrypted values corresponds to addition in plaintext. Multiplication of integral multiples in plaintext can also be performed utilizing this method.

FIG. 3C is a view illustrating an example in which an encrypted value Enc(A×B) of a value A×B is calculated while in the encrypted state. Since A×B is equivalent to adding A up a total of B times, when performing a calculation with an encrypted value, the encrypted value Enc(A×B) can be determined by multiplying the encrypted value Enc(A) by itself B times (that is, raising Enc(A) to the power of B). Naturally, it is also possible to multiply the encrypted value Enc(B) by itself A times.

Because the data that is handled according to the present embodiment is binary data, there is a risk that a fingerprint of a query will be revealed if unique ciphertext is generated with respect to plaintext, since only two kinds of encrypted values are generated, i.e. an encrypted value with respect to "1" and an encrypted value with respect to "0". A probabilistic cryptosystem is used to prevent such a disadvantage. According to a probabilistic cryptosystem, since encryption procedures are performed probabilistically, there is no leaking of partial information of any kind of the plaintext based on the ciphertext. In general, ciphertexts that are generated based on the same plaintext differ to each other. In the first to third embodiments, a Paillier cryptosystem is used as a probabilistic cryptosystem having an additive homomorphic property.

According to the present embodiment, ciphertext sent from a searcher device is handled and subjected to calculation processing while in the form of the ciphertext so that a query is not revealed to the administrator of a database. In the cryptosystem having an additive homomorphic property, however, since only an operation corresponding to addition of plaintext can be performed, a Tversky index in fractional form cannot be calculated. Therefore, the present embodiment introduces the following score T that takes a non-negative value (value that is not negative, i.e. a positive value or 0) when the Tversky index is greater than or equal to a predetermined threshold value $\theta_n/\theta_d$.

$$T_i = |p_i \cap q| \times \{\gamma(\theta_d - \theta_n) + \theta_n(\mu_a + \mu_b)\} + \theta_n\{(-|q| + \mu_b((-|p_i|)\}$$ [Equation 2]

$\theta_n$ and $\theta_d$ are natural numbers that satisfy $\theta_n \leq \theta_d$ Note that although the Paillier cryptosystem has an additive homomorphic property, $(-|q|)$ and $(-|p_i|)$ are used for performing addition of a negative value, since subtraction cannot be performed in an encrypted states.

A score $T_i$ is obtained by transforming an inequality between the Tversky index and the threshold value $\theta_n/\theta_d$.

$$S_i = \frac{|p_i \cap q|}{\frac{\mu_a}{\gamma}(|q| - |p_i \cap q|) + \frac{\mu_b}{\gamma}(|p_i| - |p_i \cap q|) + |p_i \cap q|}$$ [Equation 3]

where $\mu_a$, $\mu_b$, and $\gamma$ represent 0 or natural numbers that satisfy $$0 \leq \frac{\mu_a}{\gamma}, 0 \leq \frac{\mu_b}{\gamma}$$

$|p_i|$ represents a number of elements having a value of "1" that are included in sequence data $p_i$ $|q|$ represents a number of elements having a value of "1" that are included in sequence data q $(|p_i \cap q|)$ represents a number of elements having a value of "1" that are included in both of sequence data $p_i$ and sequence data q Note that since decimals cannot be handled according to the Paillier cryptosystem, coefficients $\alpha$ and $\beta$ of the Tversky index $S_i$ are taken as $\mu_a/\gamma$ and $\mu_b/\gamma$ and the threshold value is expressed as $\theta_n/\theta_d$.

First Embodiment

Configuration of Search System

FIG. 4 is a view illustrating the configuration of a search system of the first embodiment. The search system has a management device 10 that has a database 12 that stores fingerprints of compounds, and a searcher device 30 that transmits a query to the management device 10 to request a search of the database 12. The management device 10 and the searcher device 30 are connected by a network 50 such as the Internet.

The management device 10 has a database 12 of compounds, a query reception portion 16, an input data checking portion 18, a score encrypted value calculation portion 20, a transmission order rearranging portion 24, and a result transmission portion 26. The management device 10 also has a setting value storage portion 14 in which coefficients $\mu_a/\gamma$ and $\mu_b/\gamma$ that are used with a Tversky index and a threshold value $\theta_n/\theta_d$ for determining a similarity based on the Tversky index are stored, and a setting value changing portion 22 that changes a setting value stored in the setting value storage portion 14. Further, although not illustrated in FIG. 4, the management device 10 has a storage portion and a CPU that are used in calculating a similarity between a query q and data $p_i$ of a compound. The hardware configuration of the database is described later (see FIG. 5).

The query reception portion 16 has a function of receiving a query (search condition) transmitted from the searcher device 30. The query reception portion 16 stores the received data in the storage portion. The query includes encrypted values $Enc(q_1)$, $Enc(q_2)$, ..., $Enc(q_n)$ obtained by encrypting values of each element of a fingerprint of a compound, an encrypted value $Enc(-|q|)$ of the number of "1" values included in the fingerprint, and a public key for encryption. Note that since the respective values of the fingerprint and the number of "1" values included in the fingerprint are each encrypted, the contents thereof cannot be known by the management device 10.

The input data checking portion 18 has a function of checking whether or not a query received by the query reception portion 16 is appropriate. For example, while a value of each element of a fingerprint is obtained by encrypting a value of "1" or "0", the input data checking portion 18 can determine that a query is not appropriate if the query includes an encrypted value of a numerical value other than the aforementioned values so that processing is not performed thereafter. As described above, although the management device 10 cannot know any of the contents of the plaintext from the encrypted values, this kind of check can be implemented using technology such as, for example, zero-knowledge certification (Practical Private Computation and Zero-Knowledge Tools for Privacy-Preserving Distributed Data Mining SDM 2008: pp. 265-276; Towards restricting plaintext space in public key encryption, Proceedings of IWSEC 2011, LNCS 7038, 2011, pp. 193-209.). Note that the input data check is not essential in this configuration, and can be omitted.

The setting value storage portion 14 stores coefficients $\mu_a/\gamma$ and $\mu_b/\gamma$ that are used in the Tversky index, and a threshold value $\theta_d/\theta_n$ used in calculating a Tversky score. The setting value storage portion 14 may store any number of patterns of the coefficients $\mu_a/\gamma$ and $\mu_b/\gamma$ and the threshold value $\theta_d/\theta_n$. Thus, the coefficients $\mu_a/\gamma$ and $\mu_b/\gamma$ can be changed in accordance with the kind of search (Tanimoto coefficient, substructure search, Dice's coefficient or the like), and the threshold value $\theta_d/\theta_n$ can be changed according to the degree of similarity that is required.

The score encrypted value calculation portion 20 has a function of calculating an encrypted value of a score $T_i$ that shows whether or not a Tversky index for data $p_i$ (i=1, 2, ..., m; m is the number of data items) of compounds in the database 12 and the query q is equal to or greater than the predetermined threshold value $\theta_n/\theta_d$. At the searcher device 30, it is determined that the Tversky index is equal to or greater than the threshold value when the score $T_i$ is a non-negative value, and that the Tversky index is less than the threshold value when the score $T_i$ is a negative value. The score encrypted value calculation portion 20 calculates encrypted values of scores $T_1, T_2 ..., T_m$ for the respective compounds in the database 12. Processing to calculate an encrypted value of the score T by the score encrypted value calculation portion 20 is described later.

The transmission order rearranging portion 24 has a function of randomly rearranging the transmission order of encrypted values of a plurality of scores $T_1, T_2, ..., T_m$. Specifically, the encrypted values of the scores $T_1, T_2, ..., T_m$ are stored in advance in the storage portion in the calculated order, and the transmission order rearranging portion 24 can rearrange the transmission order of the encrypted values when performing transmission thereof by randomly reading out the encrypted values from the storage portion.

The score encrypted value calculation portion 20 reads out the data of the compounds in sequential order from the database 12 and calculates encrypted values of the scores $T_1, T_2, ..., T_m$. If the encrypted values of the scores $T_1, T_2, ..., T_m$ are transmitted in the calculated order each time, it might be possible to estimate the compounds included in the database 12 if a query on the searcher device 30 side is appropriately altered to obtain the scores $T_1, T_2, ..., T_m$. The transmission order rearranging portion 24 prevents this disadvantage. Note that this configuration is not essential, and can be omitted.

The result transmission portion 26 has a function of transmitting the encrypted values of the scores $T_1, T_2, ..., T_m$ to the searcher device 30.

Next, the configuration of the searcher device 30 will be described. The searcher device 30 has a query input portion 32, an encryption key generation portion 34, an encrypting portion 36, a query transmission portion 38, a result reception portion 40, a decrypting portion 42, a determination portion 44, a display portion 46 and a storage portion 48.

The query input portion 32 has a function of accepting input of data q of a fingerprint of a compound to which a user wants to search for similar compounds. The query input portion 32 may also accept input of a structural formula of a compound, and perform a transformation from the structural formula to a fingerprint. The query input portion 32 stores the data q of an input fingerprint in the storage portion 48. The query input portion 32 also determines the number of elements having a value of "1" included in the fingerprint, and stores the determined number of elements $|q|$ in the storage portion.

The encryption key generation portion 34 has a function of generating a public key for performing encryption utilizing the Paillier cryptosystem and a private key for decryption. The encryption key generation portion 34 stores the generated public key and private key in the storage portion. The encryption key generation portion 34 may generate a new public key and private key for each query q or may use the same public key and private key for a plurality of the queries q.

The encrypting portion 36 has a function of reading out the value of each element $q_1, q_2, ..., q_n$ of a fingerprint of a query and the number of elements $|q|$ having the value of "1" from the storage portion 48 and encrypting the respective values $q_1, q_2, ... q_n$ of the fingerprint, and also encrypting a value $(-|q|)$ that is a value obtained by attaching a minus sign to the number of elements $|q|$. A minus sign is attached to the number of elements $|q|$ here because, although the Paillier cryptosystem has an additive homomorphic property, calculation of an encrypted value that corresponds to subtraction cannot be handled in the Paillier cryptosystem, and the number of elements with a previously attached minus sign can thus be handled in addition of a negative value. The encrypting portion 36 inputs encrypted values $Enc(q_1)$, $Enc(q_2)$, ..., $Enc(q_n)$ of each element of the fingerprint and an encrypted value $Enc(-|q|)$ of the number of elements $|q|$ having the value of "1" to the query transmission portion 38.

The query transmission portion 38 has a function of transmitting the encrypted values $Enc(q_1)$, $Enc(q_2)$, ..., $Enc(q_n)$ of each element of the fingerprint, the encrypted value $Enc(-|q|)$ of the number of elements $|q|$, and the public key to the management device 10.

The result reception portion 40 has a function of receiving encrypted values of scores $T_1, T_2, ..., T_m$ that have been transmitted from the management device 10. The result reception portion 40 stores the encrypted values of the received scores $T_1, T_2, ..., T_m$ in the storage portion 48. The decrypting portion 42 has a function of using the private key to decrypt the encrypted values of the scores $T_1, T_2, ..., T_m$ that have been received by the result reception portion 40. The decrypting portion 42 inputs the scores $T_1, T_2, \ldots, T_m$ obtained by decrypting to the determination portion 44.

The determination portion 44 determines whether or not the scores $T_1, T_2, \ldots, T_m$ have a non-negative value. If the respective scores $T_1, T_2, \ldots, T_m$ have a non-negative value, it is thereby known that the Tversky index is greater than or equal to the predetermined threshold value $\theta_n/\theta_d$. By counting the number of scores $T_i$ that have a non-negative value, it can be known how many similar compounds are in the database 12 of the management device 10.

The display portion 46 has a function of displaying a determination result of the determination portion 44. The display portion 46 may display a result indicating the number of compounds for which the Tversky index is greater than or equal to the threshold value $\theta_n/\theta_d$ or may display the proportion of such compounds.

Figure 5:
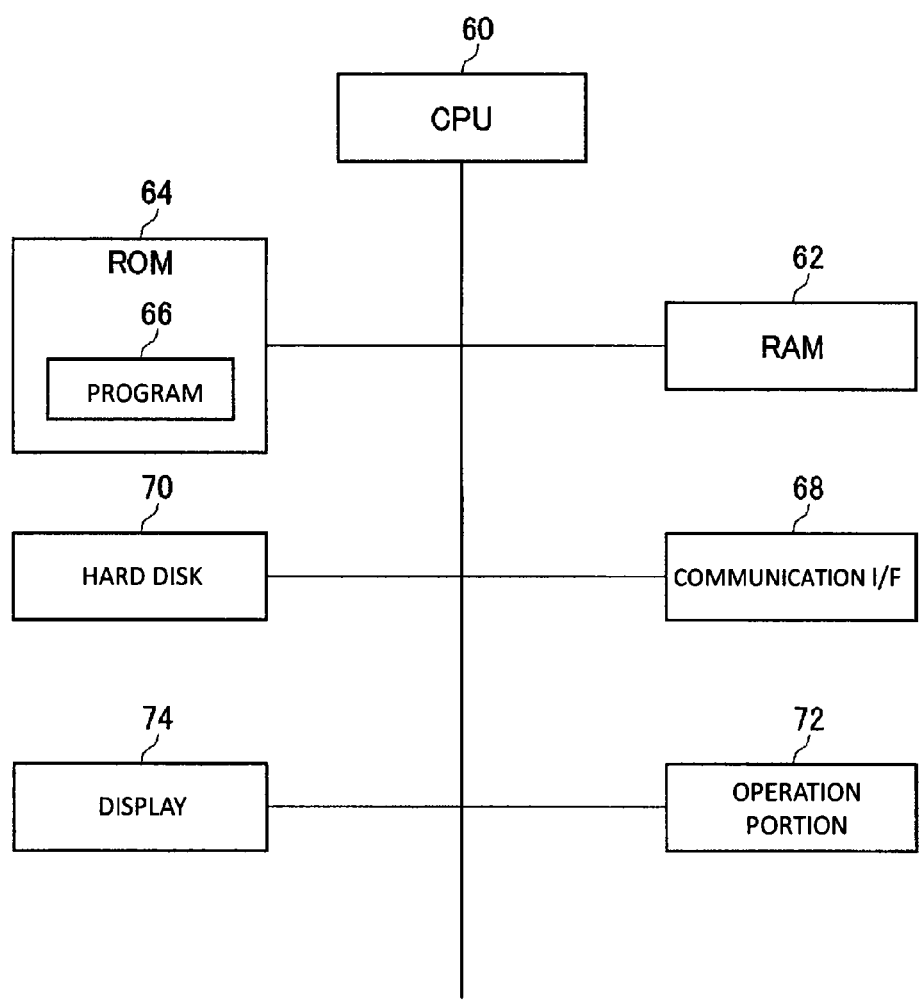
FIG. 5 is a view illustrating the hardware configuration of a management device and a searcher device.

FIG. 5 is a view illustrating the hardware configuration of the management device 10 and the searcher device 30. The management device 10 and the searcher device 30 are each constituted by a computer in which a CPU 60, a RAM 62, a ROM 64, a communication interface 68, a hard disk 70, an operation portion 72, and a display 74 are connected by a data bus 76. The contents of a program 66 that is written in the ROM 64 differ between the management device 10 and the searcher device 30. The program 66 that is stored in the ROM 64 of the management device 10 is a program for implementing the functions of the management device 10. The program 66 that is stored in the ROM 64 of the searcher device 30 is a program for implementing the functions of the searcher device 30. The respective programs 66 fall within the scope of the present invention. In the management device 10, data of fingerprints of compounds is stored on the hard disk.

[Operations of Search System]

Figure 6:
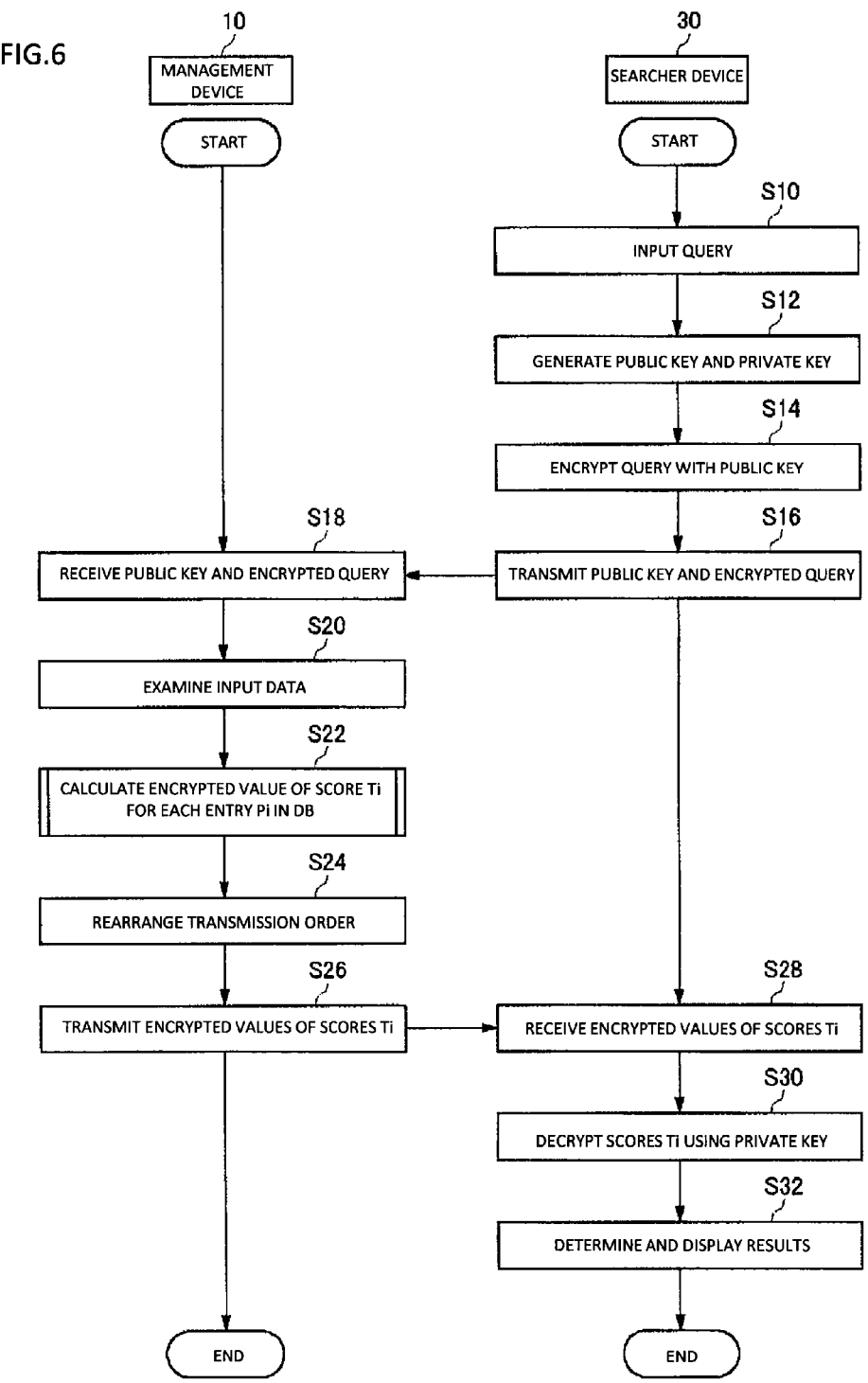
FIG. 6 is a flowchart illustrating operations of the search system according to the embodiment.

FIG. 6 is a flowchart illustrating the operations of the search system of the present embodiment. First, data q of a fingerprint of a compound that is a query is input at the searcher device 30 (S10). The searcher device 30 stores the input data q of the fingerprint in the storage portion 48. Next, the searcher device 30 generates a set of a public key and a private key of the Paillier cryptosystem, and stores the generated keys in the storage portion 48 (S12).

The searcher device 30 reads out the data q of the fingerprint that is the query from the storage portion 48, and uses the public key to encrypt the value of each element $q_1, q_2, \ldots, q_n$ of the fingerprint that has been read out (S14).

Figure 7:
FIG. 7 is a view illustrating an example in which each element of a fingerprint is encrypted and an encrypted value is determined.

FIG. 7 is a view that illustrates an example in which each element of a fingerprint is encrypted to obtain encrypted values. The searcher device 30 encrypts the value, that is, "1" or "0", of each element to obtain encrypted values $Enc(q_1)$, $Enc(q_2), \ldots, Enc(q_n)$. Since the Paillier cryptosystem that is used in the present embodiment is a probabilistic cryptosystem, the encrypted values are not the same even when the same value is encrypted. It is thus possible to prevent plaintext values from being disadvantageously predicted based on encrypted values.

The searcher device 30 determines the number of elements having the value of "1" among the elements included in the fingerprint, and encodes a value obtained by attaching a minus sign to the number of elements $|q|$ to determine an encrypted value $Enc(-|q|)$. The searcher device 30 transmits the public key, the encrypted value $Enc(-|q|)$ of the number of elements $|q|$ having the value of "1", and the encrypted values $Enc(q_1), Enc(q_2), \ldots, Enc(q_n)$ of each element of the query to the management device 10 (S16).

The management device 10 receives the public key, the encrypted value $Enc(-|q|)$, and the encrypted values $Enc(q_1)$, $Enc(q_2), \ldots, Enc(q_n)$ of each element of the query that have been transmitted from the searcher device 30 (S18), and stores the received data in the storage portion. The management device 10 validates the received data (S20). While the encrypted value of each element of the query is obtained by encrypting a value of either "1" or "0", the management device 10 stops the processing at the time when the management device 10 determines that the received data includes an encrypted value that is not "1" or "0", because the sequence data q of the query is erroneous, and notifies the searcher device 30 that there is an input error in the query q. Further, according to this configuration, it is also possible to protect the information in the database 12 from a malicious attacker (deviatory form attacker) that attempts to extract a large amount of information of the database 12 of the management device 10 by choosing an abnormal value other than the values 0 and 1 that are originally assumed as the query q.

Subsequently, the management device 10 calculates an encrypted value of the score $T_i$ based on data (respective data items are referred to as an "entry") $p_i$ of fingerprints of compounds stored in the database 12 and the query q (S22). The specific calculation method is described hereunder referring to FIG. 8 to FIG. 12.

Figure 8:
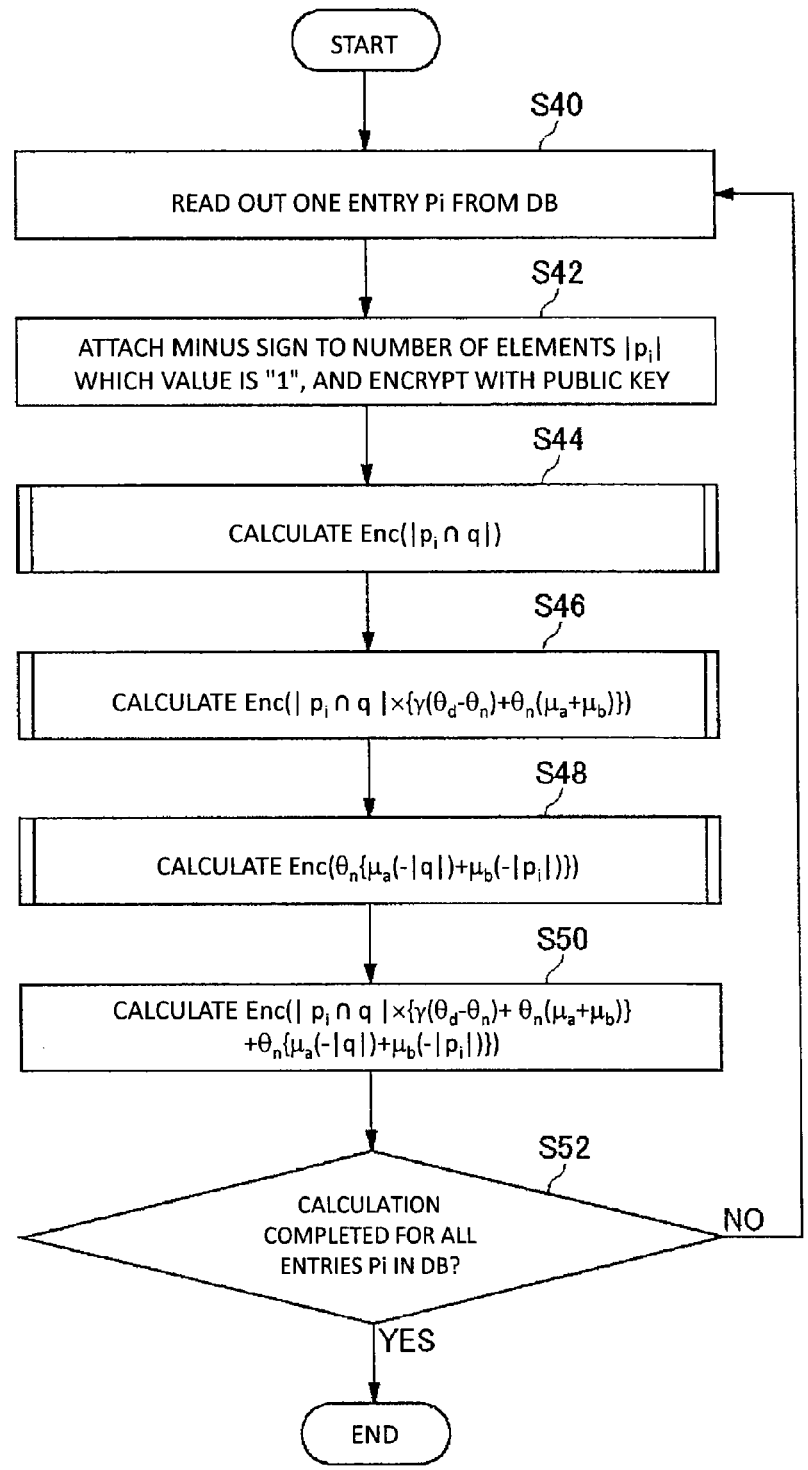
FIG. 8 is a flowchart illustrating an operation that calculates an encrypted value of a score $T_i$.

FIG. 8 is a flowchart illustrating an operation to calculate an encrypted value of the score $T_i$. First, the management device 10 reads out one entry $p_i$ from the database 12 (S40). The management device 10 stores the read entry $p_i$ in the storage portion.

The management device 10 counts the number of elements having the value of "1" among the elements included in the entry $p_i$, and encodes a value obtained by attaching a minus sign to a number of elements $|p_i|$ using a public key to determine an encrypted value $Enc(-|p_i|)$ (S42). A minus sign is attached to the number of elements $|p_i|$ here because the Paillier cryptosystem cannot perform a calculation corresponding to subtraction of plaintext in an encrypted value state. Next, the management device 10 calculates a number ($|p_i \cap q|$) of substructures that are common between the query q and the entry $p_i$ that has been read out from the database 12 while in the form of the encrypted values (S44).

Figure 9A:
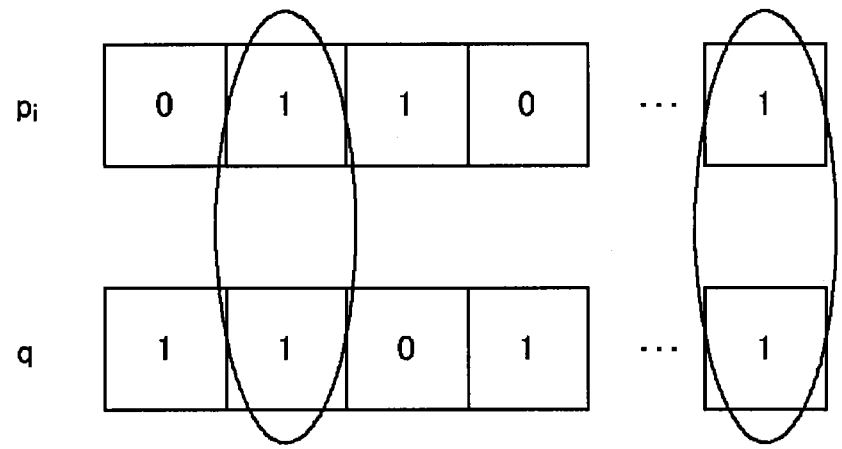
FIG. 9A is a view illustrating an example of each element of an entry $p_i$ and each element of a query q.

FIG. 9A is a view illustrating an example of each element of the entry $p_i$ and each element of the query q. Substructures that the query q and the entry $p_i$ commonly have are the elements having a value of "1" in both the entry $p_i$ and the query q. As shown by the circles surrounding values in FIG. 9A, the number of common substructures can be determined by determining the number of elements having a value of "1" in both the entry $p_i$ and the query q.

Figure 9B:
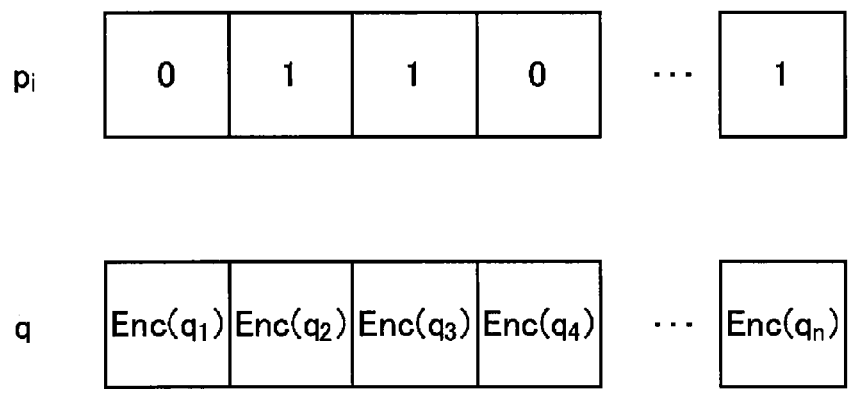
FIG. 9B is a view illustrating an example of each element of the entry $p_i$ and each element of the query q as seen from the management device.

As shown in FIG. 9B, while the management device 10 ascertains the value of each element of the entry $p_i$, the management device 10 cannot ascertain the value of each element of the query q because it is encrypted. However, when the values of elements $q_k$ of the query q that correspond to elements $p_{i,k}$ having a value of "1" in the entry $p_i$ are added up (multiplied in ciphertext), the number of elements that are common between the query q and entry $p_i$ can be determined because elements having the value of "1" in the entry $p_i$ and the value of "0" in the query q do not affect the result when they are added up.

Figure 10:
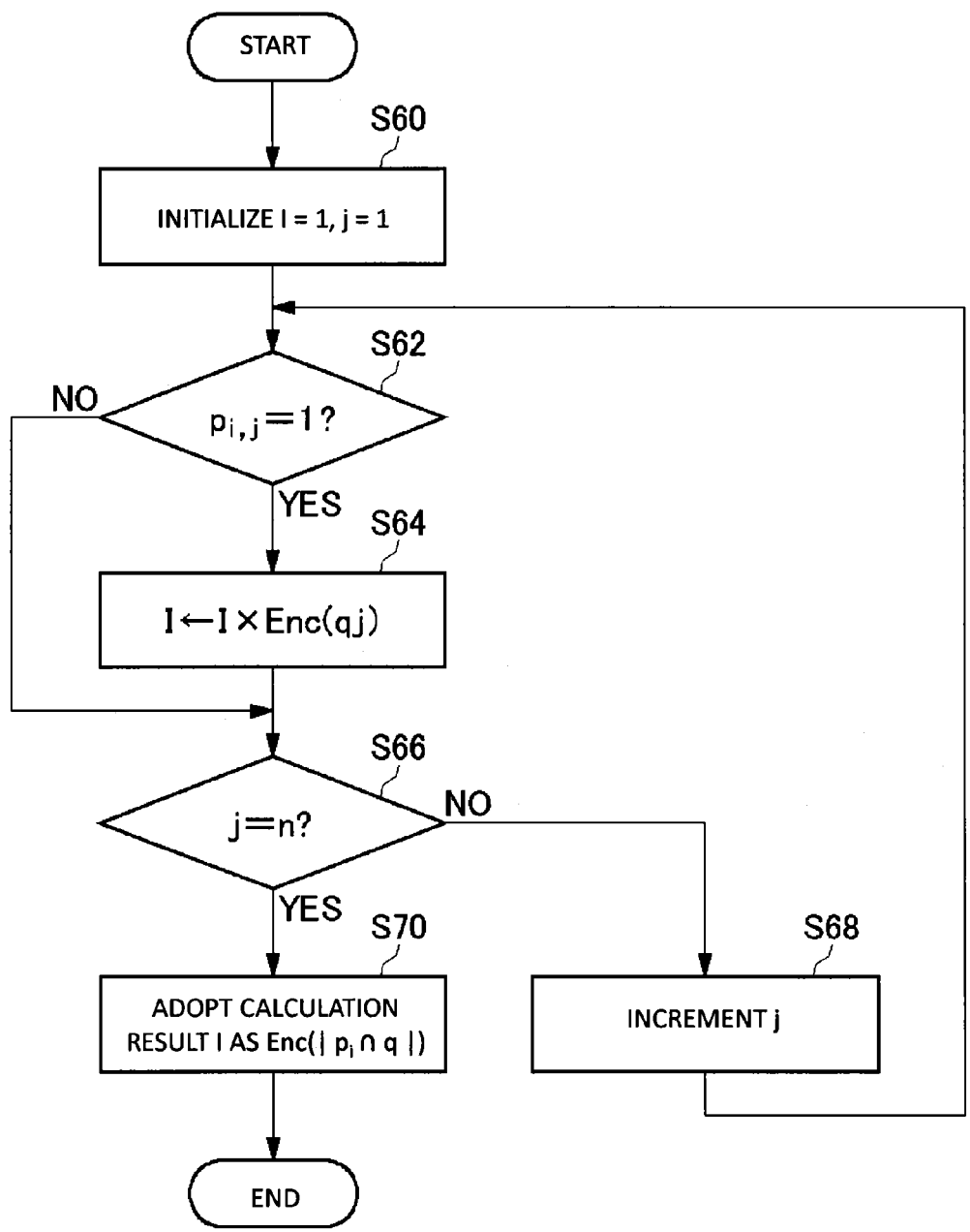
FIG. 10 is a flowchart illustrating an algorithm that determines an encrypted value of the number of elements that are common to the query q and the entry $p_i$.

FIG. 10 is a flowchart illustrating an algorithm for obtaining an encrypted value of a number of substructures that are common between the query q and the entry $p_i$ that has been read out from the database 12. First, the management device 10 initializes variables by setting a variable I and a counter j to "1" respectively (S60). The variable I is a variable into which the encrypted value of the number of elements of common substructures is entered, and the variable j is a counter. Note that when the flow of operations shown in FIG.

10 is implemented, the variable I and the counter j have their regions allocated in a portion of the RAM 62, and the values of the variable I and the counter j are stored by writing data in the relevant region. Initialization of the above described variable I and counter j refers to writing the value "1" in the predetermined region that has been allocated thereto. Note that also in the following description, for initializing a variable or performing an operation on a variable, an operation is performed utilizing hardware resources of the computer, such as the CPU 60 and the RAM 62, in accordance with the program 66 stored on the ROM 64.

The management device 10 determines whether or not the value of a first element $p_{i,1}$ of the entry $p_i$ is "1" (S62). If the value is "1" (Yes in S62), the management device 10 multiplies the encrypted value $Enc(q_j)$ of the element of the query corresponding thereto by the variable I, and assigns the obtained result to I (S64). Specifically, the management device 10 reads out the data stored in the region allocated to the variable I, multiplies the read data by the encrypted value $Enc(q_j)$, and writes the obtained result in the variable I region.

Next, the management device 10 determines whether or not the counter j=n (n represents the length of the fingerprint) (S66). If the counter j is not equal to n (No in S66), the management device 10 increments j (S68), determines whether or not the next element $p_{i,2}$ of the entry $p_i$ is "1" (S62), and repeats the above processing until the value of the counter j is equal to n. When the counter j=n (Yes in S66), the management device 10 adopts the calculation result I as an encrypted value $Enc(|p_i \cap q|)$ of the number of common elements between the query q and the entry $p_i$ (S70).

Returning to FIG. 8, the management device 10 determines an encrypted value of a value obtained by multiplying the number of elements $|p_i \cap q|$ of common substructures between the query q and the entry $p_i$ by $\{\gamma(\theta_d - \theta_n) + \theta_n(\mu_a + \mu_b)\}$. Here, $\gamma(\theta_d - \theta_n) + \theta_n(\mu_a + \mu_b)$ are each setting values, and are natural numbers that are known to the management device 10. As described above using FIG. 3C, an encrypted value of a value obtained by integral multiplication in plaintext can be obtained by exponentiation of an encrypted value. In this case, the encrypted value $Enc(|p_i \cap q|)$ is multiplied by itself $\gamma(\theta_d - \theta_n) + \theta_n(\mu_a + \mu_b)$ times.

Figure 11:
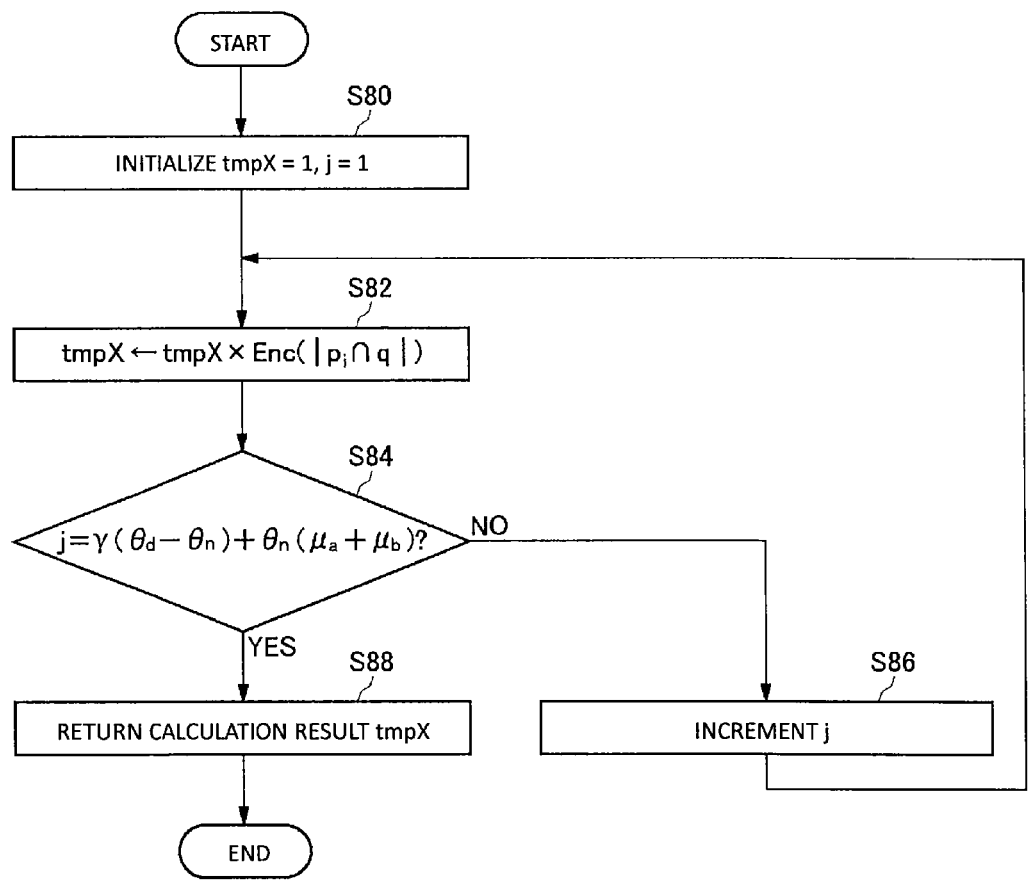
FIG. 11 is a flowchart illustrating an algorithm that calculates an encrypted value $\text{Enc}((|p_i \cap q|) \times \{\gamma(\theta_d - \theta_n) + \theta_n(\mu_a + \mu_b)\})$.

FIG. 11 is a flowchart illustrating an algorithm for calculating an encrypted value $Enc((|p_i \cap q|) \times \{\gamma(\theta_d - \theta_n) + \theta_n(\mu_a - \mu_b)\})$. First, the management device 10 encrypts variables tmpX and j (S80). The variable tmpX is a variable into which a calculation result is entered, and the variable j is a counter.

The management device 10 multiplies the variable tmpX by the encrypted value $Enc(|p_i \cap q|)$ and assigns the resulting value to the variable tmpX (S82). The management device 10 determines whether or not the counter $j=\gamma(\theta_d - \theta_n) + \theta_n(\mu_a + \mu_b)$ (S84). If the counter j is not equal to $\gamma(\theta_d - \theta_n) + \theta_n(\mu_a + \mu_b)$ (No in S84), the management device 10 increments the counter j (S86) and multiplies the variable tmpX by the encrypted value $Enc(-p_i \cap q|)$ and assign the resulting value to the variable tmpX (S82). If the counter $j=\gamma(\theta_d - \theta_n) + \theta_n(\mu_a + \mu_b)$ (Yes in S84), the management device 10 returns the determined calculation result tmpX (S88).

Returning again to FIG. 8, the management device 10 calculates $Enc(\theta_n\{\mu_a(-|q|) + \mu_b(-|p_i|)\})$. The encrypted value $Enc(-|q|)$ of the number of elements $|q|$ having the value of "1" that are included in the query q, and the encrypted value $Enc(-|p_i|)$ of the number of elements $|p_i|$ having the value of "1" that are included in the entry $p_i$ are used for this calculation.

Figure 12:
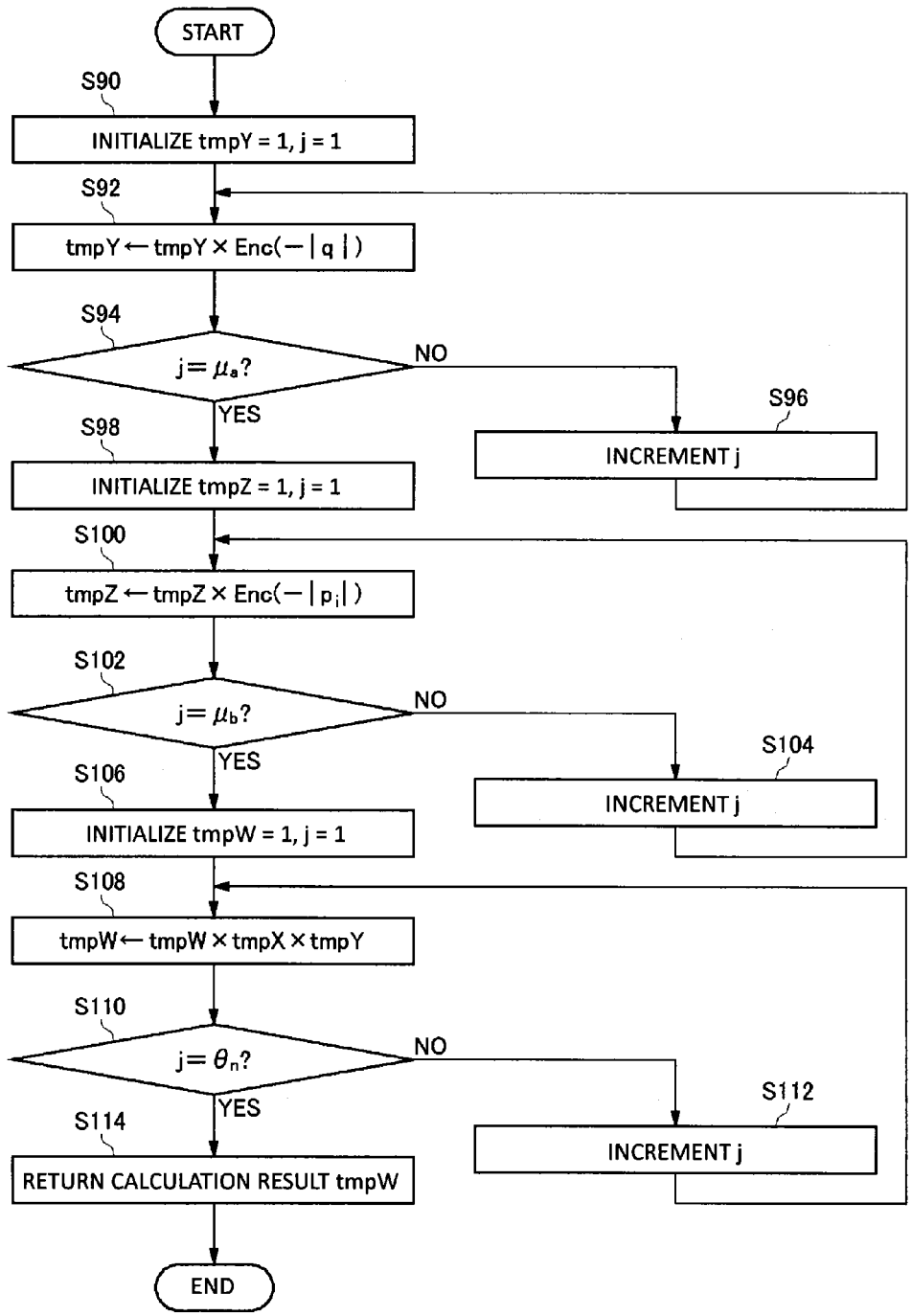
FIG. 12 is a flowchart illustrating an algorithm that calculates $\text{Enc}(\theta_n\{\mu_a(-|q|) + \mu_b(-|p_i|)\})$.

FIG. 12 is a flowchart illustrating an algorithm for calculating $Enc(\theta_n\{\mu_a(-|q|) + \mu_b(-|p_i|)\})$. First, the management device 10 sets "1" to variables tmpY and j, respectively, to initialize the variables tmpY and j (S90). The variable tmpY is a variable into which a calculation result of $Enc(\mu_a(-|q|))$ is entered, and the variable j is a counter. The management device 10 multiplies the variable tmpY by the encrypted value $Enc(-|q|)$, and assigns the resulting value to the variable tmpY (S92). The management device 10 determines whether or not the counter $j=\mu_a$ (S94). If the counter j is not equal to $\mu_a$ (No in S94), the management device 10 increments the counter j (S96), and multiplies the variable tmpY by the encrypted value $Enc(-|q|)$ and assign the resulting value to the variable tmpY. If the counter $j=\mu_a$ (Yes in S94), the management device 10 ends calculation of the encrypted value $Enc(\mu_a(-|q|))$ and proceeds to processing to calculate an encrypted value $Enc(\mu_b(-|p_i|))$.

In this case also, first, the management device 10 sets variables tmpZ and j to "1", respectively, to initialize the variables tmpZ and j (S98). The variable tmpZ is a variable into which a calculation result of the encrypted value $Enc(\mu_b(-|p_i|))$ is entered, and the variable j is a counter. The management device 10 multiplies tmpZ by the encrypted value $Enc(-|p_i|)$ and assigns the resulting value to tmpZ (S100). The management device 10 determines whether or not the counter $j=R_b$ (S102). If the counter j is not equal to $\mu_b$ (No in S102), the management device 10 increments the counter j (S104), multiply the variable tmpZ by the encrypted value $Enc(-|p_i|)$, and assign the resulting value to the variable tmpZ. If the counter $j=\mu_b$ (Yes in S102), the management device 10 ends the processing to calculate the encrypted value $Enc(\mu_b(-|p_i|))$ and proceeds to processing to calculate an encrypted value $Enc(\theta_n\{\mu_a(-|q|) + \mu_b(-|p_i|)\})$.

As described using FIG. 3C, the encrypted value $Enc(\theta_n\{\mu_a(-|q|) + \mu_b(-|p_i|)\})$ can be calculated using the $\theta_n$th power of an encrypted value $Enc(\mu_a(-|q|) + \mu_b(-|p_i|))$. Further, because the encrypted value $Enc(\mu_a(-|q|) + \mu_b(-|p_i|))$ can be calculated by multiplying the encrypted value $Enc(\mu_a(-|q|))$ by the encrypted value $Enc(\mu_b(-|p_i|))$, the encrypted value $Enc(\mu_a(-|q|) + \mu_b(-|p_i|))$ can be determined by means of tmpY×tmpZ. Accordingly, the encrypted value $Enc(\theta_n\{\mu_a(-|q|) + \mu_b(-|p_i|)\})$ can be determined by multiplying tmpY×tmpZ by itself $\theta_n$ times.

The management device 10 sets variables tmpW and j to "1", respectively, to initialize the variables tmpW and j (S106). The variable tmpW is a variable into which a calculation result of $Enc(\theta_n\{\mu_a(-|q|) + \mu_b(-|p_i|)\})$ is entered. The variable j is a counter. The management device 10 multiplies tmpW by tmpY×tmpZ, and assigns the resulting value to tmpW (S108). The management device 10 determines whether or not the counter $j=\theta_n$ (S110). If the counter j is not equal to $\theta_n$ (No in S110), the management device 10 increments the counter j (S112), multiplies the variable tmpW by tmpY×tmpZ, and assigns the resulting value to the variable tmpW. If the counter $j=\theta_n$ (Yes in S110), the management device 10 ends the processing to calculate $Enc(\theta_n\{\mu_a(-|q|) + \mu_b(-|p_i|)\})$, and returns the value of tmpW as the calculation result (S114).

Returning again to FIG. 8, the management device 10 next multiplies $Enc(|p_i \cap q| \times \{\gamma(\theta_d - \theta_n) + \theta_n(\mu_a + \mu_b)\})$ determined in step S46 by the encrypted value $Enc(\theta_n\{\mu_a(-|q|) + \mu_b(-|p_i|)\})$ determined in step S48 to determine an encrypted value $Enc(|p_i \cap q| \times \{\gamma(\theta_d - \theta_n) + \theta_n(\mu_a + \mu_b)\} + \theta_n\{\mu_a(-|q|) + \mu_b(-|p_i|)\})$.
This value is the encrypted value of the score $T_i$. The management device 10 stores the determined encrypted value of the score $T_i$ in the storage portion.

The management device 10 determines whether or not calculation of an encrypted value of the score $T_i$ is completed for all of the entries $p_i$ in the database 12 (S52). If calculation is not completed for all of the entries $p_i$ (No in S52), the management device 10 reads out the next entry $p_i$ from the database 12, calculates an encrypted value of the score $T_i$ with respect to the entry $p_i$ that has been read out and the query q, and stores the calculation result in sequential order in the storage portion. When calculation is completed for all the entries $p_i$ (i=1, 2, ..., m) (Yes in S52), the management device 10 ends calculation of the score $T_i$. The processing to calculate the score $T_i$ has been described in detail above.

The description will now return to FIG. 6 to continue the description of the operations of the search system. After rearranging the order of encrypted values of the scores $T_1$, $T_2$, ..., $T_m$ that have been determined for each entry $p_i$ in the database 12 (S24), the management device 10 transmits the encrypted values to the searcher device 30 (S26). Specifically, the transmission order rearranging portion 24 rearranges the transmission order by reading out encrypted values of scores $T_i$ at random from the storage portion and inputting the read data to the result transmission portion 26.

When the searcher device 30 receives the encrypted values of the scores $T_1, T_2, ..., T_m$ transmitted from the management device 10 (S28), the decrypting portion 42 reads out the private key from the storage portion 48 and decrypts the encrypted values of the scores $T_1, T_2, ..., T_m$ using the private key (S30). After decrypting the scores $T_1, T_2, ..., T_m$, the searcher device 30 determines if the respective scores $T_1, T_2, ..., T_m$ that have been obtained are non-negative or negative, and displays the determination result (S32). When the scores $T_1, T_2, ..., T_m$ are non-negative, it means that the Tversky index is greater than or equal to the predetermined threshold value $\theta_n/\theta_d$. Accordingly, if the database 12 includes many compounds for which the score $T_i$ is non-negative, it is thus found that the database 12 includes many similar compounds to the compound of the query. The configuration and operations of the search system according to the first embodiment have been described above.

According to the search system of the first embodiment, since the searcher device 30 transmits an encrypted value of a fingerprint of a compound that is a query to the management device 10, it is possible to examine how many similar compounds thereto are included in the database 12 while maintaining the confidentiality of the compound in the query with respect to the management device 10. Furthermore, for the management device 10, information regarding similar compounds can be advantageously notified without disclosing the compounds that are stored in the database 12.

Second Embodiment

A search system according to a second embodiment will now be described. Although the basic configuration of the search system of the second embodiment is the same as that of the first embodiment, according to the second embodiment the confidentiality of the database 12 is further enhanced by disrupting the score $T_i$ so that the absolute value of the score $T_i$ does not have a meaning.

Figure 13:
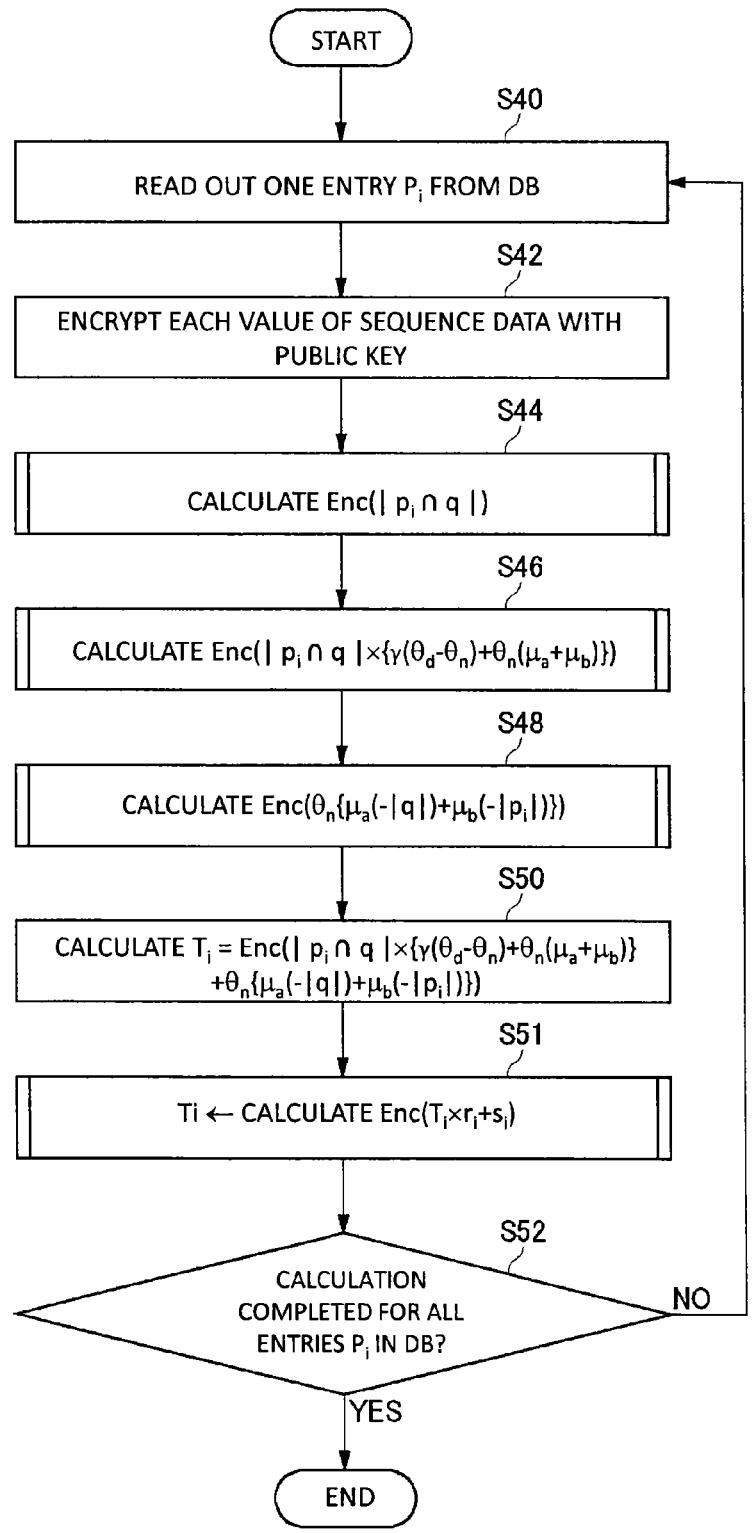
FIG. 13 is a flowchart illustrating operations of a search system according to a second embodiment.

FIG. 13 is a flowchart illustrating operations of the search system of the second embodiment. Although the operations of the search system of the second embodiment are basically the same as in the first embodiment, an encrypted value $Enc(T_i \times r_i + s_i)$ is calculated using random numbers $r_i$ and $s_i$ ($r_i > s_i$) with respect to an encrypted value $Enc(T_i)$ of the score $T_i$ determined in step S50, and the calculation result is adopted as a new score $T_i$ (S51).

Figure 14:
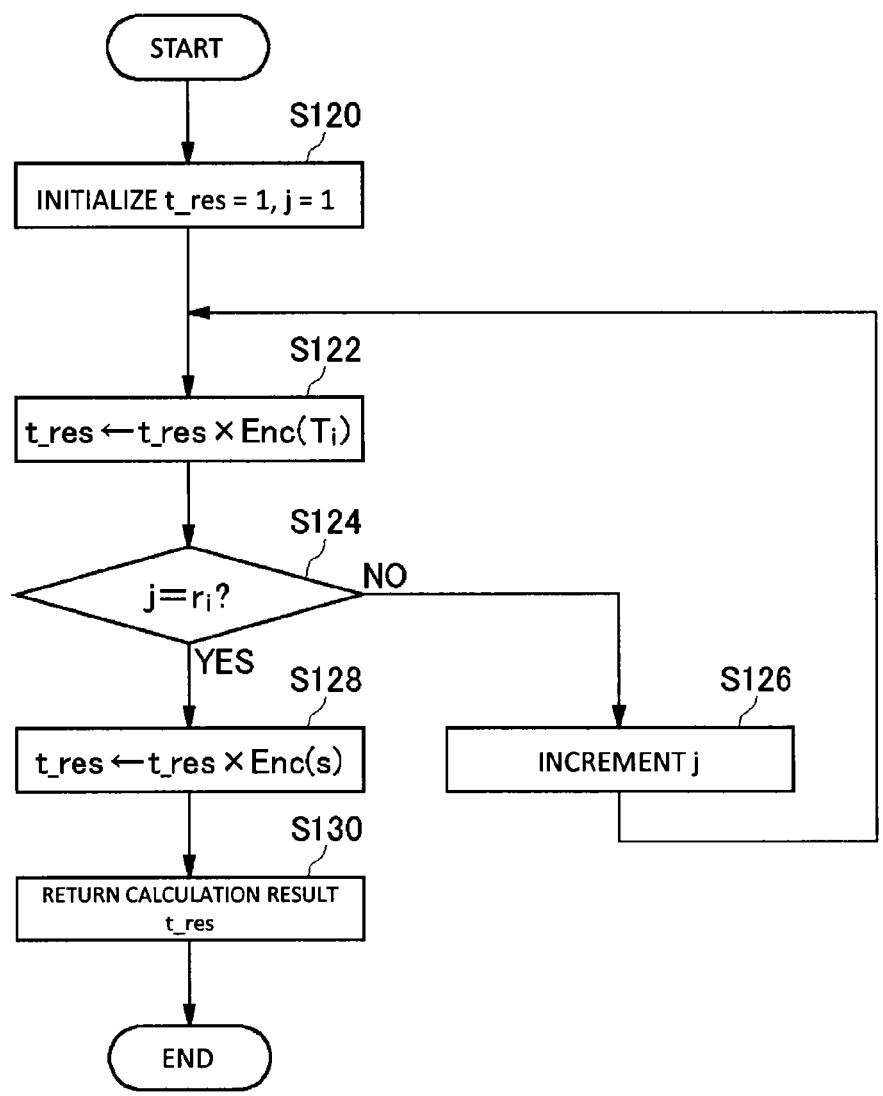
FIG. 14 is a flowchart illustrating an algorithm that calculates an encrypted value $\text{Enc}(T_i \times r_i + s_i)$.

FIG. 14 is a flowchart illustrating an algorithm for calculating the encrypted value $Enc(T_i r_i + s_i)$. The management device 10 assigns "1" to variables t_res and j, respectively, to initialize the variables t_res and j (S120). The variable t-res is a variable into which the calculation result of $Enc(T_i r_i + s_i)$ is entered, and the variable j is a counter. The management device 10 multiplies t_res by the encrypted value $Enc(T_i)$, and assigns the result to t_res (S122).

The management device 10 determines whether or not the counter j=$r_i$ (S124). If the counter j is not equal to $r_i$ (No in S124), the management device 10 increments the counter j (S126), multiplies the variable t_res by the encrypted value $Enc(T_i)$, and assigns the resulting value to the variable t_res. If the counter j=$r_i$ (Yes in S124), the management device 10 multiplies t_res by an encrypted value $Enc(s_i)$ obtained by encoding the random number $s_i$ with the public key, and assigns the resulting value to the variable t_res (S128). The management device 10 returns the calculation result t_res (S130).

The differences of the search system of the second embodiment from the search system of the first embodiment have been described above. In the second embodiment, a value obtained by multiplying the score $T_i$ by a random number $r_i$ and thereafter adding a random number $s_i$ is adopted as a new score $T_i$. Accordingly, the correlation between the degree of similarity and the score Ti disappears, and it is not possible to surmise a tendency of data stored in the database 12 based on the score $T_i$. Therefore, the confidentiality of the data stored in the database 12 can be further enhanced.

Note that the score $T_i$ indicates that the Tversky index is greater than or equal to a predetermined threshold value when the $T_i$ score is a non-negative value, and indicates that the Tversky index is lower than the predetermined threshold value when the $T_i$ score is a negative value, and only holds a meaning in terms of being a positive or negative value. Accordingly, since the positiveness or negativeness of the $T_i$ score does not change even when the $T_i$ score is multiplied by $r_i$, there is no change of any kind in the determination criterion of the score $T_i$.

In this connection, if the score $T_i$ is 0, it means that a compound for which the Tversky index matches the threshold value $\theta_n/\theta_d$ is present in the database 12. The random number $s_i$ is added to ensure that information on the presence of a compound that matches the above Tversky index is not divulged. This is because the above described disruption by the random number $r_i$ multiplication is meaningless when the score $T_i$ is 0. As a result, the score $T_i$ of a compound for which the Tversky index matches the threshold value $\theta_n/\theta_d$ is always a positive value. Note that because the random number $s_i$ is a smaller value than the random number $r_i$, the positiveness or negativeness of the $T_i$ score does not change to the other as the result of adding the random number $s_i$. This is because, in a case where the absolute value among negative scores $T_i$ is the minimum "−1", a value obtained by multiplying by $r_i$ is −$r_i$, and even if the random number $s_i$ the absolute value of which is smaller than $r_i$ is added thereto, the result remains a negative value.

Third Embodiment

A search system according to a third embodiment will now be described. Although the basic configuration of the search system of the third embodiment is the same as that of the first embodiment, according to the third embodiment the confidentiality of the database 12 is further enhanced by disrupting the score $T_i$ to generate a random share $R_i$.

Figure 15:
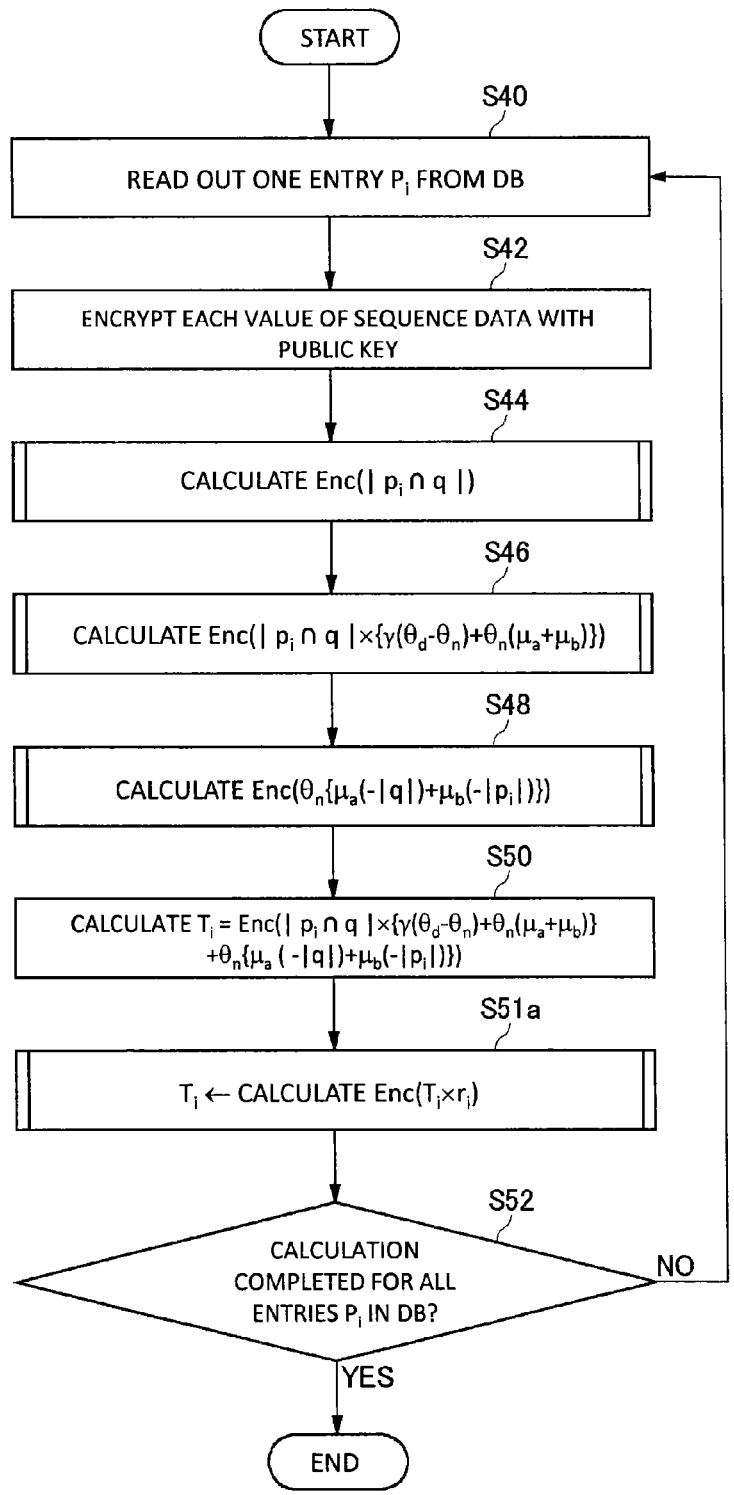
FIG. 15 is a flowchart illustrating operations of a search system according to a third embodiment.

FIG. 15 is a flowchart illustrating operations of the search system of the third embodiment. Although the operations of the search system of the third embodiment are basically the same as in the first embodiment, an encrypted value $Enc(T_i + r_i)$ is calculated using a random number $r_i$ with respect to an encrypted value Enc($T_i$) of the score $T_i$ determined in step S50, and the calculation result is adopted as an encrypted value of a random share $R_i$ (S51a). Since the random share $R_i$ is a value obtained by adding the random number $r_i$ to the score $T_i$, matching of the positiveness or negativeness of the Tversky index, the threshold value $\theta_n/\theta_d$, and the score $T_i$ is not guaranteed.

Figure 16:
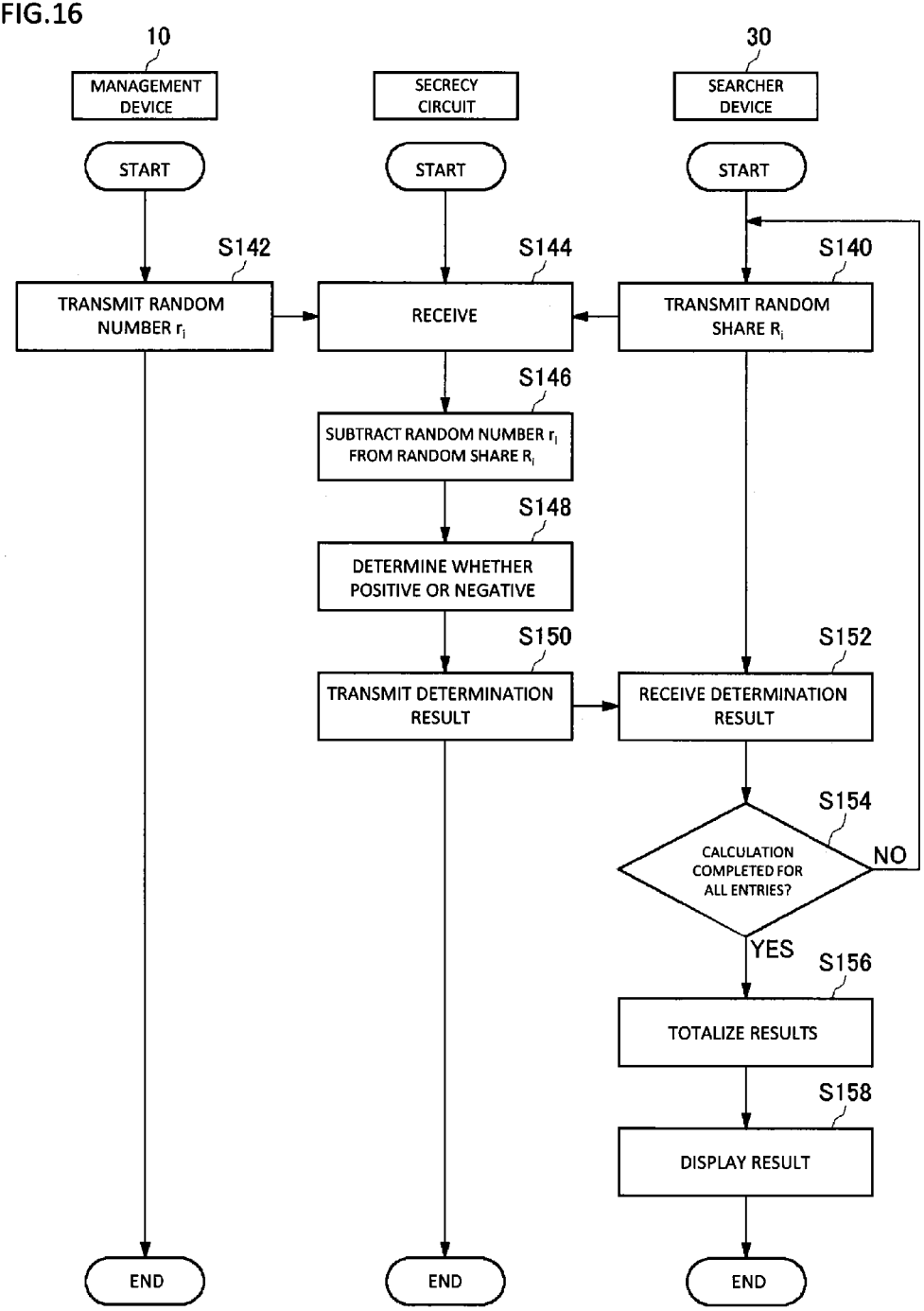
FIG. 16 is a flowchart illustrating an operation that acquires information showing whether a score $T_i$ is non-negative or negative based on a random share $R_i$.

FIG. 16 is a flowchart illustrating an operation to acquire information regarding whether the score $T_i$ is non-negative or negative based on the random share $R_i$. The searcher device 30 transmits the random share $R_i$ to a secrecy circuit (S140), and the secrecy circuit receives the random share $R_i$ (S144). Here, the term "secrecy circuit" refers to a circuit that can perform calculations while keeping the contents of the calculations secret, and is designed using secure function evaluation.

The management device 10 transmits a random number $r_i$ used in generating the random share $R_i$ transmitted from the searcher device 30 to the secrecy circuit (S142), and the secrecy circuit receives the random number $r_i$ (S144). The secrecy circuit obtains the score $T_i$ by subtracting the random number $r_i$ from the random share $R_i$ (S146), and determines whether the score $T_i$ is non-negative or negative (S148).

Note that transmitting of the random share $R_i$ and the random number $r_i$ (S140 to S144), subtraction of the random number $r_i$ from the random share $R_i$ (S146), and determining whether the score $T_i$ is non-negative or negative (S148) are performed using secure function evaluation.

The secrecy circuit transmits the result of determination as to whether the score $T_i$ is non-negative or negative to the searcher device 30 (S150), and the searcher device 30 receives the determined result (S152). The searcher device 30 determines whether or not calculation is completed for all entries (S154). If calculation is not completed for all entries (No in S154), the searcher device 30 repeats the same processing as described above for the next random share $R_i$. When calculation is completed for all entries (Yes in S154), the searcher device 30 totalizes the determination results (S156), and displays the results (S158).

The differences of the search system of the third embodiment from the search system of the first embodiment have mainly been described above. In the third embodiment, the random share $R_i$, instead of the score $T_i$, is returned to the searcher device 30, and by transmitting the random share $R_i$ to the secrecy circuit, the searcher device 30 obtains only a determination result as to whether or not the score $T_i$ is non-negative. Since there is no correlation between the degree of similarity and the score Ti, it is not possible to surmise a tendency of data stored in the database 12 based on the random share $R_i$.

Fourth Embodiment

A search system according to a fourth embodiment will now be described. Although in the first to third embodiments, an example using the Paillier cryptosystem that is a cryptosystem having an additive homomorphic property has been described, the fourth embodiment uses a cryptosystem that has a multiplicative homomorphic property in addition to an additive homomorphic property. The basic configuration of the search system of the fourth embodiment is the same as in the first to third embodiments (see FIG. 4 and the like). According to the fourth embodiment, since properties of the cryptosystem that is used are different, processing in the score encrypted value calculation portion 20 in the management device 10 is different from the processing in the first to third embodiments.

Figure 17:
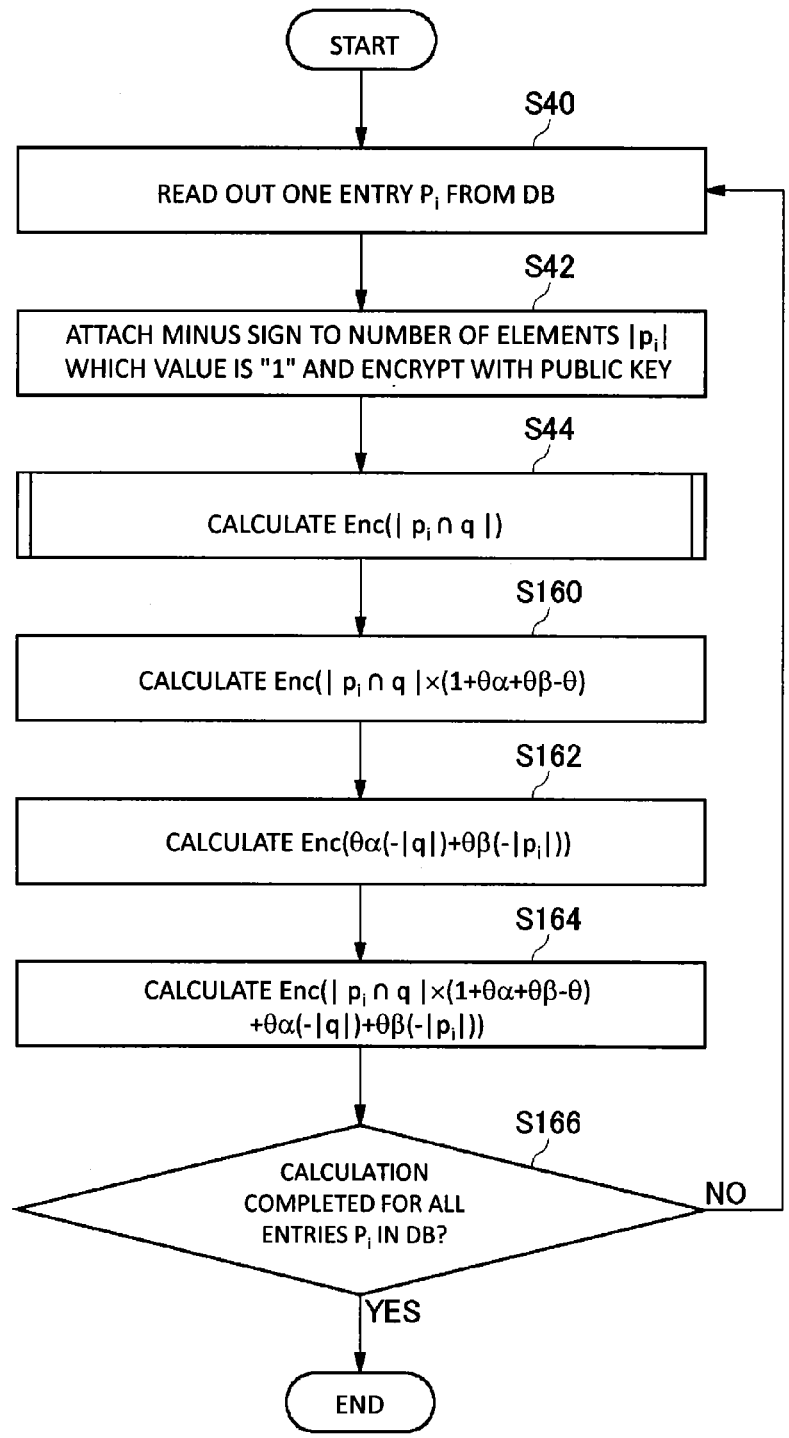
FIG. 17 is a view illustrating operations of a score encrypted value calculation portion according to a fourth embodiment.

FIG. 17 is a flowchart illustrating operations of the score encrypted value calculation portion 20 in the fourth embodiment. Steps (S40-S44) in which the number of elements of substructures that are common between the query q and the read entry $p_i$ is determined are the same as in the first to third embodiments.

According to the fourth embodiment, the cryptosystem has a multiplicative homomorphic property, and since multiplication of plaintext can be performed while in the form of an encrypted value, the following equation is used as the score $T_i$.

$$T_i = |p_i \cap q| \times (1+\theta\alpha+\theta\beta-\theta) + (-|q|) \times \theta\alpha + (-|p_i|) \times \theta\beta \quad \text{[Equation 4]}$$

where $\alpha$ and $\beta$ represent Tversky index setting values and $\theta$ represents a threshold value $|p_i|$ represents a number of elements having a value of "1" that are included in sequence data $p_i$ $|q|$ represents a number of elements having a value of "1" that are included in sequence data q $(|p_i \cap q|)$ represents a number of elements having a value of "1" that are included in both of sequence data $p_i$ and sequence data q According to the fourth embodiment, the score encrypted value calculation portion 20 calculates an encrypted value Enc($|p_i \cap q| \times (1+\theta\alpha+\beta-\theta)$) (S160). Since the cryptosystem has a multiplicative homomorphic property, the encrypted value Enc($|p_i \cap q| \times (1+\theta\alpha+\theta\beta-\theta)$) can be determined by performing a calculation corresponding to a calculation of $|p_i \cap q| \times (1+\theta\alpha+\theta\beta-\theta)$ in plaintext. Processing that multiplies the encrypted value Enc($|p_i \cap q|$) by itself $(1+\theta\alpha+\theta\beta-\theta)$ times in the first to third embodiments is unnecessary, and calculation is also possible even when $(1+\theta\alpha+\theta\beta-\theta)$ is not a natural number.

Next, the score encrypted value calculation portion 20 calculates an encrypted value Enc($\theta\alpha(-\mu q\mu)+\theta\beta(-|p_i|)$) (S162). First, the score encrypted value calculation portion 20 performs a calculation corresponding to $(-|q|) \times \theta\alpha$ in plaintext on the encrypted value Enc($-|q|$) and an encrypted value Enc($\theta\alpha$) obtained by encrypting $\theta\alpha$ with the public key, and determines Enc($\theta\alpha(-|q|)$). Next, the score encrypted value calculation portion 20 performs a calculation corresponding to $(-|p_i|) \times \theta\beta$ in plaintext on the encrypted value Enc($-|p_i|$) and an encrypted value Enc($\theta\beta$) obtained by encrypting op with the public key, and determines Enc($\theta\beta(-|p_i|)$). The score encrypted value calculation portion 20 then performs a calculation corresponding to $(\theta\alpha(-|q|))+(\theta\beta(-|p_i|))$ in plaintext on the encrypted value Enc($\theta\alpha(-|q|)$) and the encrypted value Enc($\theta\beta(-|p_i|)$) to determine Enc($\theta\alpha(-|q|)+(\theta\beta(-p_i|)$).

Thereafter, the score encrypted value calculation portion 20 calculates an encrypted value Enc($|p_i \cap q| \times (1+\theta\alpha+\theta\beta-\theta) + \theta\alpha(-|q|)+(\theta\beta(-|p_i|)$) of the score $T_i$ (S164). Specifically, the score encrypted value calculation portion 20 performs a calculation corresponding to $|p_i \cap q| \times (1+\theta\alpha+\theta\beta-\theta)+\theta\alpha(-|q|)+(\theta\beta(-|p_i|))$ in plaintext on the encrypted value Enc($|p_i \cap q| \times (1+\theta\alpha+\theta\beta-\theta)$) and the encrypted value Enc($\theta\alpha(-|q|)+(\theta\beta(-|p_i|)$). Thus, the score $T_i$ with respect to the entry $p_i$ that has been read out from the database 12 and the query q is determined.

The score encrypted value calculation portion 20 determines whether or not calculation of the score $T_i$ is completed for all of the entries $p_i$ in the database 12 (S166). If the calculation has not been completed for all of the entries $p_i$ (No in S166), the score encrypted value calculation portion 20 reads out an entry $p_i$ for which the score $T_i$ has not been calculated from the database 12 and performs the same processing as described above. When calculation has been completed for all of the entries $p_i$ (Yes in S166), the score encrypted value calculation portion 20 ends the processing.

The difference between the search system of the fourth embodiment and the first to third embodiment has been described above. Since the search system of the fourth embodiment uses a cryptosystem that has a multiplicative homomorphic property in addition to an additive homomorphic property, the score $T_i$ can be easily calculated.

Note that an example that uses the coefficients α and β and the threshold value θ as they are is described according to the above described embodiment based on the premise that the cryptosystem can handle decimals. In a case, however, where the cryptosystem that is used cannot handle decimals in nature, similarly to the first to third embodiments, coefficients $\mu_a/\gamma$ and $\mu_b/\gamma$ may be substituted for the coefficients α and β, respectively, and the threshold value θ may be replaced with $\theta_n/\theta_d$ to determine the score $T_i$ similar to those in the first to third embodiments.

Fifth Embodiment

A search system according to a fifth embodiment will now be described. According to the search system of the fifth embodiment, when search results are transmitted from the management device 10 to the searcher device 30, the management device 10 transmits data in which encrypted values of dummy scores $Td_i$ (i=1, 2, . . . , k) are mixed into the search results in addition to encrypted values of scores $T_i$ (i=1, 2, . . . , m) of entries $P_i$ in the database 12 to further decrease the risk of leaking information of the database 12 of the management device 10.

Figure 18:
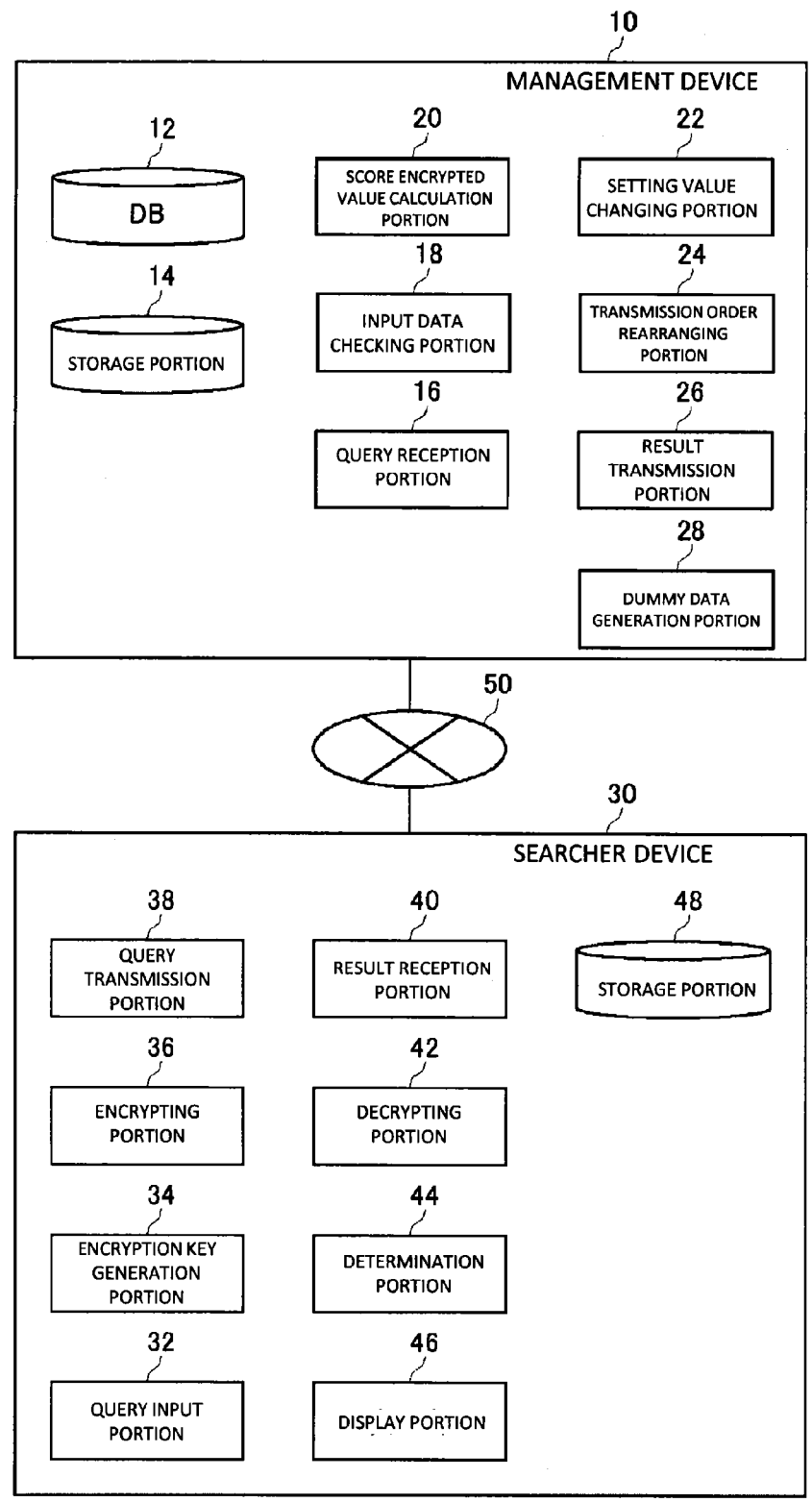
FIG. 18 is a view illustrating the configuration of a search system according to a fifth embodiment.

FIG. 18 is a view illustrating the configuration of the search system of the fifth embodiment. According to the fifth embodiment, in addition to the configuration of the search system of the first embodiment (see FIG. 4), the management device 10 comprises a dummy data generation portion 28 that generates dummy data.

The dummy data generation portion 28 generates dummy scores $Td_i$ in accordance with a predetermined probability distribution. The dummy data generation portion 28 generates data that is close to the data of the actual scores $T_i$. The dummy data generation portion 28 encrypts the generated dummy scores $Td_i$ using the public key transmitted from the searcher device 30 to generate encrypted values of the dummy scores $Td_i$. Further, the dummy data generation portion 28 determines how many non-negative dummy scores and how many negative dummy scores are included in generated dummy scores $Td_i$, and passes the determined values to the result transmission portion 26.

The transmission order rearranging portion 24 randomly rearranges (shuffles) the transmission order of encrypted values of the scores $T_i$ of the entries $P_i$ in the database 12 and the encrypted values of the dummy scores $Td_i$. The result transmission portion 26 transmits the number of non-negative dummy scores and the number of negative dummy scores to the searcher device 30 together with the encrypted values of the scores $T_i$ and the encrypted values of the dummy scores $Td_i$.

When the searcher device 30 receives the encrypted values of the scores $T_1, T_2, \ldots, T_m$ and the dummy scores $Td_1, Td_2, \ldots, Td_k$ that have been transmitted in random transmission order from the management device 10, the decrypting portion 42 reads out the private key from the storage portion 48 and decrypts the received encrypted values using the private key. Because the transmission order is random, the searcher device 30 does not know which values are the scores $T_i$ corresponding to the entries $P_i$ in the database 12 and which values are the dummy scores $Td_i$. The searcher device 30 determines whether the respective scores $T_1, T_2, \ldots, T_m$ and $Td_1, Td_2, \ldots, Td_k$ that have been obtained after decrypting are non-negative or negative, to thereby determine how many non-negative scores and negative scores are included therein. Next, the searcher device 30 subtracts the number of non-negative dummy scores and the number of negative dummy scores that have been transmitted from the management device 10 from the determined number of non-negative scores and negative scores, respectively, to thereby determine how many entries $P_i$ having a non-negative Tversky index and how many entries $P_i$ having a negative Tversky index, respectively, the database 12 includes. For example, in a case where the searcher device 30 determines based on the decrypted results of the received scores that there are 20 non-negative scores and 100 negative scores, and the number of non-negative dummy scores is assumed to be 5 and the number of negative dummy scores is assumed to be 10, the searcher device 30 can determine that there are 15 entries that have a non-negative score and 90 entries that have a negative score in the database 12. The configuration and operations of the search system of the fifth embodiment have been described above.

In the search system of the fifth embodiment, which scores are scores $T_i$ that are based on entries $P_i$ in the database 12 is concealed by the dummy scores $Td_i$ and cannot be directly known, so that the amount of information revealed to the searcher device 30 can be reduced. In addition, by increasing the number of dummy scores $Td_i$ it is possible to reduce without limit the amount of superfluous information that is revealed to the searcher device 30 to nearly zero.

Although the search system and search method of the present invention have been described in detail above by way of the embodiments, the present invention is not limited to the above described embodiments.

Although examples in which the management device 10 and the searcher device 30 are connected through the network 50 such as the Internet are described in the foregoing embodiments, the network 50 that connects the management device 10 and the searcher device 30 may be any kind of network. Further, it is not necessarily the case that the management device 10 and the searcher device 30 are always connected by the network 50, and query data q that has been output at the searcher device 30 may be recorded on a recording medium such as a CD-ROM, the CD-ROM may then be forwarded by mail to the operator of the management device 10, and the operator may cause the management device 10 to read the CD-ROM.

Although examples that use the Paillier cryptosystem as an encryption scheme that has an additive homomorphic property and a property as a probabilistic cryptosystem are described in the foregoing embodiments, any encryption scheme may be used in the present invention as long as the encryption scheme satisfies the condition of having an additive homomorphic property and a property as a probabilistic cryptosystem.

With respect to the Paillier scheme, since the Paillier scheme itself does not allow encryption when plaintext is a negative value, the following processing is performed when applying the Paillier scheme to the present invention. Specifically, a numerical value range from 0 to n that can be handled by the Paillier cryptosystem is divided in half, and the values from 0 to n/2 are taken as they are as positive values corresponding to 0 to n/2, while the values from n/2+1 to n are considered to be negative values that correspond to −1 to −n/2. This method is common practice for enabling handling of minus signs.

Although examples in which the number of similar compounds present in a database is examined are described in the foregoing embodiments, the present invention is not limited to compounds and can be applied to any database in which the structure of a substance or the presence or absence of a property is expressed with binary data. For example, it is possible to use the present invention to examine how many similar gene sequences are present in a database. In a case where genetic information of an individual is submitted as a query, the present invention is useful since it is necessary to conceal the genetic information from the viewpoint of protecting personal information.

INDUSTRIAL APPLICABILITY

According to the present invention, it is possible to examine how many data items that are similar to a query are included in a database while maintaining the confidentiality of the database and the query. Thus, the present invention is useful for searching for similar compounds of a novel compound in drug discovery and for searching for genetic information and the like.

REFERENCE SIGNS LIST

10 Management device
12 Database
14 Storage portion
16 Query reception portion
18 Input data checking portion
20 Score encrypted value calculation portion
22 Setting value changing portion
24 Transmission order rearranging portion
26 Result transmission portion
28 Dummy data generation portion
30 Searcher device
32 Query input portion
34 Encryption key generation portion
36 Encrypting portion
38 Query transmission portion
40 Result reception portion
42 Decrypting portion
44 Determination portion
46 Display portion
48 Storage portion
50 Network
60 CPU
62 RAM
64 ROM
66 Program
68 Communication interface
70 Hard disk
72 Operation portion
74 Display

The invention claimed is:
1. A search method involving a management device having a database that stores data representing a substructure or a property of a substance, and a searcher device for inputting a search condition and outputting a search result of the database, the data being sequence data in which, with respect to a predetermined plurality of substructures or properties, "1" is set in a case where a substance has the substructure or property, and "0" is set in a case where the substance does not have the substructure or property,
wherein the search method being for examining whether the database includes sequence data $p_i$ (i=1, 2, ..., m; m represents a number of sequence data items) for which a Tversky index $S_i$

$$S_i = \frac{|p_i \cap q|}{\frac{\mu_a}{\gamma}(|q| - |p_i \cap q|) + \frac{\mu_b}{\gamma}(|p_i| - |p_i \cap q|) + |p_i \cap q|}$$ [Equation 5]

where $\mu_a$, $\mu_b$, and $\gamma$ represent 0 or natural numbers that satisfy $$0 \leq \frac{\mu_a}{\gamma}, 0 \leq \frac{\mu_b}{\gamma}$$

$|p_i|$ represents a number of elements having a value of "1" that are included in sequence data $p_i$
$|q|$ represents a number of elements having a value of "1" that are included in sequence data q
($|p_i \cap q|$) represents a number of elements having a value of "1" that are included in both of sequence data $p_i$ and sequence data q
is greater than or equal to a threshold value $\theta_n/\theta_d$ (where $\theta_n$ and $\theta_d$ are natural numbers that satisfy $\theta_n \leq \theta_d$) with respect to query sequence data q that represents a substructure or a property of a substance that is input as a search condition at the searcher device and sequence data $p_i$ of a substance stored in the database, the search method comprising the following steps:
(1) the searcher device generates a public key and a private key of a cryptosystem having an additive homomorphic property;
(2) the searcher device accepts input of query sequence data q;
(3) the searcher device determines a number of elements $|q|$ having a value of "1" among elements constituting the query sequence data q, encrypts a value obtained by attaching a minus sign to the number of elements $|q|$ with the public key, and encrypts a value of each element $q_j$ (where j=1, ..., n; n represents a length of the query sequence q) of the query sequence data q with the public key;
(4) the searcher device outputs the public key, the encrypted value Enc(-|q|), and encrypted values Enc($q_1$), Enc($q_2$), ..., Enc($q_n$) of each element of the query sequence data q to the management device;
(5) the management device receives the public key, the encrypted value Enc(-|q|), and the encrypted values Enc($q_1$), Enc($q_2$), ..., Enc($q_n$) of each element of the query sequence data q that are output from the searcher device;
(6) the management device reads out one item of sequence data $p_i$ from the database;
(7) the management device determines a number of elements $|p_i|$ having a value of "1" among elements constituting the sequence data $p_i$, and encrypts a value obtained by attaching a minus sign to the number of elements $|p_i|$ with the public key;
(8) the management device examines each element $p_{i,j}$ (where j=0, 1, ..., n; n represents a length of the sequence data $p_i$) of the sequence data $p_i$, utilizes the additive homomorphic property of the cryptosystem to perform on an encrypted value Enc($q_k$) a calculation corresponding to addition in plaintext of all elements $q_k$ (k satisfies $p_{i,k}$=1) of the query sequence data q that correspond to elements having a value of "1" in the sequence data $p_i$, and determines an encrypted value $Enc(|p_i \cap q|)$ of a number of elements $|p_i \cap q|$ having a value of "1" in both of the query sequence data q and the sequence data $p_i$;

(9) the management device utilizes the additive homomorphic property of the cryptosystem to perform a calculation corresponding to a calculation in which $(|p_i \cap q|)$ is added up $\{\gamma(\theta_d - \theta_n) + \theta_n(\mu_a - \mu_b)\}$ times in plaintext on the encrypted value $Enc(|p_i \cap q|)$, and determines an encrypted value $Enc((|p_i \cap q|) \times \{\gamma(\theta_d - \theta_n) + \theta_n(\mu_a - \mu_b)\})$;

(10) the management device utilizes the additive homomorphic property of the cryptosystem to perform a calculation corresponding to a calculation in which $(-|q|)$ is added up $\mu_a$ times in plaintext on the encrypted value $Enc(-|q|)$ to determine an encrypted value $Enc(\mu_a(-|q|))$, performs a calculation corresponding to a calculation in which $(-|p_i|)$ is added up $\mu_b$ times in plaintext on the encrypted value $Enc(-|p_i|)$ to determine an encrypted value $Enc(\mu_b(-|p_i|))$, performs a calculation corresponding to $\mu_a(-|q|) + \mu_b(-|p_i|)$ in plaintext on the encrypted value $Enc(\mu_a(-|q|))$ and the encrypted value $Enc(\mu_b(-|p_i|))$ to determine an encrypted value $Enc(\mu_a(-|q|) + \mu_b(-|p_i|))$, and further performs a calculation corresponding to a calculation in which $(\mu a(-|q|) + \mu b(-|pi|))$ is added up $\theta n$ times in plaintext on the encrypted value $Enc(\mu_a(-|q|) + \mu_b(-|p_i|))$ to determine an encrypted value $Enc(\theta_n(\mu_a(-|q|) + \mu_b(-|p_i|)))$;

(11) the management device utilizes the additive homomorphic property of the cryptosystem to perform a calculation corresponding to $(|p_i \cap q|) \times \{\gamma(\theta_d - \theta_n) + \theta_n(\mu_a + \mu_b)\} + \theta_n(\mu_a(-|q|) + \mu_b(-|p_i|))$ in plaintext on the encrypted value $Enc((|p_i \cap q|) \times \{\gamma(\theta_d - \theta_n) + \theta_n(\mu_a + \mu_b)\}$ determined in the above (9) and the encrypted value $Enc(\theta_n(\mu_a(-|q|) + \mu_b(-|p_i|)))$ determined in the above (10), and determines an encrypted value $Enc((|p_i \cap q|) \times \{\gamma(\theta_d - \theta_n) + \theta_n(\mu_a + \mu_b) + \theta_n(\mu_a(-|q|) + \mu_b(-|p_i|))\})$ as an encrypted value of a score $T_i$;

(12) the management device repeats the above (6) to (11) for each of a plurality of items of sequence data $p_i$ included in the database, and determines an encrypted value of the score $T_i$ for each of the items of sequence data $p_i$;

(13) the management device outputs encrypted values of the scores $T_1, T_2, \ldots, T_m$ to the searcher device;

(14) the searcher device receives the encrypted values of the scores $T_1, T_2, \ldots, T_m$ that are output from the management device;

(15) the searcher device decrypts the encrypted values of the scores $T_1, T_2, \ldots, T_m$ with the private key;

(16) the searcher device determines whether the scores $T_1, T_2, \ldots, T_m$ are non-negative or negative; and

(17) the searcher device outputs a determination result.

2. The search method according to claim 1, wherein the cryptosystem is a probabilistic cryptosystem.

3. The search method according to claim 1, wherein the calculation corresponding to addition in plaintext is multiplication in cases of an encrypted value.

4. The search method according to claim 1, comprising a step in which the management device utilizes the additive homomorphic property of the cryptosystem to perform a calculation corresponding to a calculation in which $(|p_i \cap q|) \times \{\gamma(\theta_d - \theta_n) + \theta_n(\mu_a + \mu_b)\} + \theta_n(\mu_a(-|q|) + \mu_b(-|p_i|))$ is added up r times (r represents a random number) in plaintext on the encrypted value of the score $T_i$ determined in the above (11), and adopts a determined encrypted value $Enc([(|p_i \cap q|) \times \{\gamma(\theta_d - \theta_n) + \theta_n(\mu_a + \mu_b) + \theta_n(\mu_a(-|q|) + \mu_b(-|p_i|))\}] \times r)$ as an encrypted value of the score $T_i$.

5. The search method according to claim 4, comprising a step in which the management device encrypts a value $(-s_i)$ (where $s_i$ is a natural number that satisfies $r_i > s_i$) with the public key to obtain an encrypted value $Enc(-s_i)$, and utilizes the additive homomorphic property of the cryptosystem to perform a calculation corresponding to $[(|p_i \cap q|) \times \{\gamma(\theta_d - \theta_n) + \theta_n(\mu_a + \mu_b) + \theta_n(\mu_a(-|q|) + \mu_b(-|p_i|))\}] \times r_i + (-s_i)$ in plaintext with respect to an encrypted value $Enc(((|p_i \cap q|) \times \{\gamma(\theta_d - \theta_n) + \theta_n(\mu_a + \mu_b) + \theta_n(\mu_a(-|q|) + \mu_b(-|p_i|))\}) \times r_i)$ and the encrypted value $Enc(-s_i)$, and adopts a determined encrypted value $Enc([(|p_i \cap q|) \times \{\gamma(\theta_d - \theta_n) + \theta_n(\mu_a + \mu_b) + \theta_n(\mu_a(-|q|) + \mu_b(-|p_i|))\}] \times r_i) - s_i)$ as an encrypted value of the score $T_i$.

6. The search method according to claim 1, wherein the management device encrypts a random number $r_i$ with the public key to obtain an encrypted value $Enc(r_i)$, utilizes the additive homomorphic property of the cryptosystem to perform a calculation corresponding to $(|p_i \cap q|) \times \{\gamma(\theta_d - \theta_n) + \theta_n(\mu_a + \mu_b)\} + \theta_n(\mu_a(-|q|) + \mu_b(-|p_i|)) + r_i$ in plaintext on the encrypted value of the score $T_i$ determined in the above (11) and the encrypted value $Enc(r_i)$, and determines an encrypted value $Enc((|p_i \cap q|) \times \{\gamma(\theta_d - \theta_n) + \theta n(\mu_a + \mu_b) + \theta_n(\mu_a(-|q|) + \mu_b(-|p_i|))\} + r)$ as an encrypted value of a random share $R_i$, wherein, in the step of determining whether the scores $T_1, T_2, \ldots, T_m$ are non-negative or negative in the above (16):

(16-1) the searcher device transmits the random share $R_i$ to a secrecy circuit that is designed using secure function evaluation;

(16-2) the management device transmits the random number $r_i$ to the secrecy circuit;

(16-3) the secrecy circuit subtracts the random number $r_i$ from the random share $R_i$ and determines whether a determined value is non-negative or negative; and (16-4) the secrecy circuit transmits a result of determination as to whether the determined value is non-negative or negative to the searcher device.

7. The search method according to claim 1, wherein in the above (13), the management device outputs encrypted values of the scores $T_1, T_2, \ldots, T_m$ in an order that is different from an order of data stored in the database.

8. The search method according to claim 1, comprising a step in which the searcher device accepts input of any of coefficients $\mu_a/\gamma$ and $\mu_b/\gamma$ and a value $\theta_n/\theta_d$ that are included in the Tversky index $S_i$, and a step in which the searcher device outputs to the management device any of the coefficients $\mu_a/\gamma$ and $\mu_b/\gamma$ and the value $\theta_n/\theta_d$ that are input.

9. The search method according to claim 1, comprising:

a step in which the management device generates dummy scores $Td_1, Td_2, \ldots, Td_k$ and encrypts the generated dummy scores $Td_1, Td_2, \ldots, Td_k$ with the public key; and a step in which the management device randomly rearranges an output order of encrypted values of the dummy scores $Td_1, Td_2, \ldots, Td_k$ and encrypted values of the scores $T_1, T_2, \ldots, T_m$;

wherein, in the above (13), the management device transmits the randomly rearranged encrypted values and data showing a number of non-negative dummy scores and a number of negative dummy scores included in the dummy scores to the searcher device.

10. The search method according to claim 1, comprising a step in which the management device determines whether or not an encrypted value $Enc(q_i)$ of each element of the query sequence data q transmitted from the searcher device is an encrypted value obtained by encrypting "1" or "0", and if the query sequence data q includes an encrypted value that is not an encrypted value obtained by encrypting "1" or "0", the management device ends the search without performing subsequent processing.

11. A search method involving a management device having a database that stores data representing a substructure or a property of a substance, and a searcher device for inputting a search condition and outputting a search result of the database, the data being sequence data in which, with respect to a predetermined plurality of substructures or properties, "1" is set in a case where a substance has the substructure or property, and "0" is set in a case where the substance does not have the substructure or property, wherein the search method being for examining whether the database includes sequence data $p_i$, (i=1, 2, ..., m; m represents a number of sequence data items) for which a Tversky index $S_i$ $$S_i = \frac{|p_i \cap q|}{\alpha(|q| - |p_i \cap q|) + \beta(|p_i| - |p_i \cap q|) + |p_i \cap q|} \quad \text{[Equation 6]}$$

where $\alpha$ and $\beta$ satisfy $0 \leq \alpha$ and $0 \leq \beta$ $|p_i|$ represents a number of elements having a value of "1" that are included in sequence data $p_i$ $|q|$ represents a number of elements having a value of "1" that are included in sequence data q $(|p_i \cap q|)$ represents a number of elements having a value of "1" that are included in both of sequence data $p_i$ and sequence data q is greater than or equal to a threshold value $\theta(0<\theta \leq 1)$ with respect to query sequence data q that represents a substructure or a property of a substance that is input as a search condition at the searcher device and sequence data $p_i$ of a substance stored in the database, the search method comprising the following steps:

(1) the searcher device generates a public key and a private key of a cryptosystem having a multiplicative homomorphic property and an additive homomorphic property;

(2) the searcher device accepts input of query sequence data q;

(3) the searcher device determines a number of elements $|q|$ having a value of "1" among elements constituting the query sequence data q, encrypts a value obtained by attaching a minus sign to the number of elements with the public key, and encrypts a value of each element $q_j$ (where j=1, ..., n; n represents a length of the query sequence q) of the query sequence data q with the public key;

(4) the searcher device outputs the public key, the encrypted value $Enc(-|q|)$, and encrypted values $Enc(q_1), Enc(q_2), ..., Enc(q_n)$ of each element of the query sequence data q to the management device;

(5) the management device receives the public key, the encrypted value $Enc(-|q|)$, and the encrypted values $Enc(q_1), Enc(q_2), ..., Enc(q_n)$ of each value of the query sequence data q that are output from the searcher device;

(6) the management device reads out one item of sequence data $p_i$ from the database;

(7) the management device determines a number of elements $|p_i|$ having a value of "1" among elements constituting the sequence data $p_i$, and encrypts a value obtained by attaching a minus sign to the number of elements $|p_i|$ with the public key to obtain an encrypted value $Enc(-|p_i|)$;

(8) the management device examines each element $p_{i,j}$ (where j=0, 1, ..., n; n represents a length of the sequence data $p_i$) of the sequence data $p_i$, utilizes the additive homomorphic property of the cryptosystem to perform on an encrypted value $Enc(q_k)$ a calculation corresponding to addition in plaintext of all elements $q_k$ (k satisfies $p_{i,k}=1$) of the query sequence data q that correspond to elements having a value of "1" in the sequence data $p_i$, and determines an encrypted value $Enc(|p_i \cap q|)$ of a number of elements $|p_i \cap q|$ having a value of "1" in both of the query sequence data q and the sequence data $p_i$;

(9) the management device encodes a value $(1+\theta\alpha+\theta\beta-\theta)$ with the public key to determine an encrypted value $Enc(1+\theta\alpha+\theta\beta-\theta)$, and utilizes the multiplicative homomorphic property of the cryptosystem to perform a calculation corresponding to $(|p_i \cap q|) \times (1+\theta\alpha+\theta\beta-\theta)$ in plaintext on the encrypted value $Enc(|p_i \cap q|)$ and the encrypted value $Enc(1+\theta\alpha+\theta\beta-\theta)$ to determine an encrypted value $Enc((|p_i \cap q|) \times (1+\theta\alpha+\theta\beta-\theta))$;

(10) the management device encrypts a value $\theta\alpha$ and a value $\theta\beta$ with the public key to determine an encrypted value $Enc(\theta\alpha)$ and an encrypted value $(\theta\beta)$ and utilizes the multiplicative homomorphic property of the cryptosystem to perform a calculation corresponding to $-|q| \times \theta\alpha$ in plaintext on the encrypted value $Enc(-|q|)$ and the encrypted value $Enc(\theta\alpha)$ to determine an encrypted value $Enc(-|q| \times \theta\alpha)$, and further performs a calculation corresponding to $-|p_i| \times \theta\beta$ in plaintext on the encrypted value $Enc(+|p_i|)$ and the encrypted value $Enc(\theta\beta)$ to determine an encrypted value $Enc(-|p_i| \times \theta\beta)$ and utilizes the additive homomorphic property of the cryptosystem to perform a calculation corresponding to $(-|q| \times \theta\alpha) + (-|p_i| \times \theta\beta)$ in plaintext on the encrypted value $Enc(-|q| \times \theta\alpha)$ and the encrypted value $Enc(-|p_i| \times \theta\beta)$ to determine an encrypted value $Enc((-|q| \times \theta\alpha) + (-|p_i| \times \theta\beta))$;

(11) the management device utilizes the additive homomorphic property of the cryptosystem to perform a calculation corresponding to $(|p_i \cap q|) \times (1+\theta\alpha+\theta\beta-\theta) + (-|p_i| \times \theta\alpha) + (-|p_i| \times \theta\beta)$ in plaintext on the encrypted value $Enc(|p_i \cap q|) \times (1+\theta\alpha+\theta\beta-\theta))$ determined in the above (9) and the encrypted value $Enc((-|q| \times \theta\alpha) + (-|p_i| \times \theta\beta))$ determined in the above (10), and determines an encrypted value $Enc(|p_i \cap q|) \times (1+\theta\alpha+\theta\beta-\theta) + (-|q| \times \theta\alpha) + (-|p_i| \times \theta\beta))$ as an encrypted value of a score $T_i$;

(12) the management device repeats the above (6) to (11) for each item of sequence data $p_i$ of a plurality of substances included in the database, and determines an encrypted value of the score $T_i$ for each of the items of sequence data $p_i$;

(13) the management device outputs encrypted values of the scores $T_1, T_2, ..., T_m$ to the searcher device;

(14) the searcher device receives the encrypted values of the scores $T_1, T_2, ..., T_m$ that are output from the management device;

(15) the searcher device decrypts the encrypted values of the scores $T_1, T_2, ..., T_m$ with the private key;

(16) the searcher device determines whether the scores $T_1, T_2, ..., T_m$ are non-negative or negative; and

(17) the searcher device outputs a determination result.

12. A search method in which a management device having a database that stores data representing a substructure or a property of a substance performs a search based on a search condition that is input at a searcher device, the data being sequence data in which, with respect to a predetermined plurality of substructures or properties, "1" is set in a case where a substance has the substructure or property, and "0" is set in a case where the substance does not have the substructure or property, wherein the management device returns to the searcher device an encrypted value of a score $T_i$ that, by means of whether a value thereof is non-negative or negative, indicates whether or not a Tversky index $S_i$ $$S_i = \frac{|p_i \cap q|}{\frac{\mu_a}{\gamma}(|q|-|p_i \cap q|)+\frac{\mu_b}{\gamma}(|p_i|-|p_i \cap q|)+|p_i \cap q|} \quad [\text{Equation 7}]$$

where $\mu_a$, $\mu_b$, and $\gamma$ represent 0 or natural numbers that satisfy, $$0 \leq \frac{\mu_a}{\gamma}, 0 \leq \frac{\mu_b}{\gamma}$$

$|p_i|$ represents a number of elements having a value of "1" that are included in sequence data $p_i$ $|q|$ represents a number of elements having a value of "1" that are included in sequence data q $(|p_i \cap q|)$ represents a number of elements having a value of "1" that are included in both of sequence data $p_i$ and sequence data q is greater than or equal to a threshold value $\theta_n/\theta_d$ (where $\theta_n$ and $\theta_d$ are natural numbers that satisfy $\theta_n \leq \theta_d$) with respect to query sequence data q that represents a substructure or a property of a substance that is input as a search condition at the searcher device and sequence data $p_i$, (i=1, 2, ..., m; m represents a number of sequence data items) of a substance stored in the database, the search method comprising the following steps:

(1) the management device receives a public key of a cryptosystem having an additive homomorphic property that is generated at the searcher device, an encrypted value Enc(−|q|) obtained by encrypting with the public key a value obtained by attaching a minus sign to a number of elements |q| having a value of "1" among elements constituting the query sequence data q, and encrypted values Enc($q_1$), Enc($q_2$), . . . , Enc($q_n$) obtained by encrypting each element of the query sequence data q with the public key;

(2) the management device reads out one item of sequence data $p_i$ from the database;

(3) the management device determines a number of elements $|p_i|$ having a value of "1" among elements constituting the sequence data $p_i$, and encrypts a value obtained by attaching a minus sign to the number of elements $|p_i|$ with the public key;

(4) the management device examines each element $p_{i,j}$ (where j=0, 1, . . . , n; n represents a length of the sequence data $p_i$) of the sequence data $p_i$, utilizes the additive homomorphic property of the cryptosystem to perform on an encrypted value Enc($q_k$) a calculation corresponding to addition in plaintext of all elements $q_k$ (k satisfies $p_{i,k}=1$) of the query sequence data q that correspond to elements having a value of "1" in the sequence data $p_i$, and determines an encrypted value Enc($|p_i \cap q|$) of a number of elements $|p_i \cap q|$ having a value of "1" in both of the query sequence data q and the sequence data $p_i$;

(5) the management device utilizes the additive homomorphic property of the cryptosystem to perform a calculation corresponding to a calculation in which ($|p_i \cap q|$) is added up $\{\gamma(\theta_d-\theta_n)+\theta_n(\mu_a+\mu_b)\}$ times in plaintext on the encrypted value Enc($|p_i \cap q|$), and determines an encrypted value Enc$(($|p_i \cap q|$)\times\{\gamma(\theta_d-\theta_n)+\theta_n(\mu_a+\mu_b)\})$;

(6) the management device utilizes the additive homomorphic property of the cryptosystem to perform a calculation corresponding to a calculation in which (−|q|) is added up $\mu_a$ times in plaintext on the encrypted value Enc(−|q|) to determine an encrypted value Enc($\mu_a$(−|q|)), performs a calculation corresponding to a calculation in which (−|$p_i$|) is added up $\mu_a$ times in plaintext on the encrypted value Enc(−|q|) to determine an encrypted value Enc($\mu_a$(+|q|)), performs a calculation corresponding to in which (−|$p_i$|) in plaintext on the encrypted value Enc($\mu_a$(−|q|)) and the encrypted value Enc($\mu_b$(−|$p_i$|)) to determine an encrypted value Enc($\mu_a$(−|q|)+$\mu_b$(−|$p_i$|)), and further performs a calculation corresponding to a calculation in which ($\mu_a$(−|q|)+$\mu_b$(−|$p_i$|)) is added up $\theta_n$ times in plaintext on the encrypted value Enc($\mu_a$(−|q|)+$\mu_b$(−|$p_i$|)) to determine an encrypted value Enc($\theta_n$($\mu_a$(−|q|)+$\mu_b$(−|$p_i$|)));

(7) the management device utilizes the additive homomorphic property of the cryptosystem to perform a calculation corresponding to $(|p_i \cap q|)\times\{\gamma(\theta_d-\theta_n)+\theta_n(\mu_a+\mu_b)\}+\theta_n(\mu_a(-|q|)+\mu_b(-|p_i|))$ in plaintext on the encrypted value Enc$((|p_i \cap q|)\times\{\gamma(\theta_d-\theta_n)+\theta_n(\mu_a+\mu_b)\})$ determined in the above (5) and the encrypted value Enc($\theta_n$($\mu_a$(−|q|)+$\mu_b$(−|$p_i$|))) determined in the above (6), and determines an encrypted value Enc$((|p_i \cap q|)\times\{\gamma(\theta_d-\theta_n)+\theta_n(\mu_a+\mu_b)+\theta_n(\mu_a(-|q|)+\mu_b(-|p_i|))\})$ as an encrypted value of the score $T_i$;

(8) the management device repeats the above (2) to (7) for each of a plurality of items of sequence data $p_i$ included in the database, and determines an encrypted value of the score $T_i$ for each of the items of sequence data $p_i$; and (9) the management device outputs encrypted values of the scores $T_1, T_2, \ldots, T_m$ to the searcher device.

13. A search method in which a management device having a database that stores data representing a substructure or a property of a substance performs a search based on a search condition that is input at a searcher device, the data being sequence data in which, with respect to a predetermined plurality of substructures or properties, "1" is set in a case where a substance has the substructure or property, and "0" is set in a case where the substance does not have the substructure or property, wherein the management device returns to the searcher device an encrypted value of a score $T_i$ that, by means of whether a value thereof is non-negative or negative, indicates whether or not a Tversky index $S_i$ $$S_i = \frac{|p_i \cap q|}{\alpha(|q|-|p_i \cap q|)+\beta(|p_i|-|p_i \cap q|)+|p_i \cap q|} \quad [\text{Equation 8}]$$

where $\alpha$ and $\beta$ satisfy $0 \leq \alpha$ and $0 \leq \beta$ $|p_i|$ represents a number of elements having a value of "1" that are included in sequence data $p_i$ $|q|$ represents a number of elements having a value of "1" that are included in sequence data q $(|p_i \cap q|)$ represents a number of elements having a value of "1" that are included in both of sequence data $p_i$, and sequence data q is greater than or equal to a threshold value $\theta$ ($0<\theta \leq 1$) with respect to query sequence data q that represents a substructure or a property of a substance that is input as a search condition at the searcher device and sequence data $p_i$ (i=1, 2, . . . , m; m represents a number of sequence data items) of a substance stored in the database, the search method comprising the following steps:

(1) the management device receives a public key of a cryptosystem having a multiplicative homomorphic property and an additive homomorphic property that is generated at the searcher device, an encrypted value $Enc(-|q|)$ obtained by encrypting with the public key a value obtained by attaching a minus sign to a number of elements $|q|$ having a value of "1" among elements constituting the query sequence data q, and encrypted values $Enc(q_1), Enc(q_2), \ldots, Enc(q_n)$ obtained by encrypting each element of the query sequence data q with the public key;

(2) the management device reads out one item of sequence data $p_i$ from the database;

(3) the management device determines a number of elements $|p_i|$ having a value of "1" among elements constituting the sequence data $p_i$, and encrypts a value obtained by attaching a minus sign to the number of elements $|p_i|$ with the public key to obtain an encrypted value $Enc(-|p_i|)$;

(4) the management device examines each element $p_{i,j}$ (where j=0, 1, ..., n; n represents a length of the sequence data $p_i$) of the sequence data $p_i$, utilizes the additive homomorphic property of the cryptosystem to perform on an encrypted value $Enc(q_k)$ a calculation corresponding to addition in plaintext of all elements $q_k$ (k satisfies $p_{i,k}=1$) of the query sequence data q that correspond to elements having a value of "1" in the sequence data $p_i$, and determines an encrypted value $Enc(|p_i \cap q|)$ of a number of elements $|p_i \cap q|$ having a value of "1" in both of the query sequence data q and the sequence data $p_i$;

(5) the management device encodes a value $(1+\theta\alpha+\theta\beta-\theta)$ with the public key to determine an encrypted value $Enc(1+\theta\alpha+\theta\beta-\theta)$, and utilizes the multiplicative homomorphic property of the cryptosystem to perform a calculation corresponding to $(|p_i \cap q|) \times (1+\theta\alpha+\theta\beta-\theta)$ in plaintext on the encrypted value $Enc(|p_i \cap q|)$ and the encrypted value $Enc(1+\theta\alpha+\theta\beta-\theta)$ to determine an encrypted value $Enc((|p_i \cap q|) \times (1+\theta\alpha+\theta\beta-\theta))$;

(6) the management device encrypts a value $\theta\alpha$ and a value $\theta\beta$ with the public key to determine an encrypted value $Enc(\theta\alpha)$ and an encrypted value $(\theta\beta)$ and utilizes the multiplicative homomorphic property of the cryptosystem to perform a calculation corresponding to $-|q| \times \theta\alpha$ in plaintext on the encrypted value $Enc(-|q|)$ and the encrypted value $Enc(\theta\alpha)$ to determine an encrypted value $Enc(-|q| \times \theta\alpha)$, and further performs a calculation corresponding to $-|p_i| \times \theta\beta$ in plaintext on the encrypted value $Enc(-|p_i|)$ and the encrypted value $Enc(\theta\beta)$ to determine an encrypted value $Enc(-|p_i| \times \theta\beta)$ and utilizes the additive homomorphic property of the cryptosystem to perform a calculation corresponding to $(-|q| \times \theta\alpha) + (-|p_i| \times \theta\beta)$ in plaintext on the encrypted value $Enc(-|q| \times \theta\alpha)$ and the encrypted value $Enc(-|p_i| \times \theta\beta)$ to determine an encrypted value $Enc((-|q| \times \theta\alpha) + (|p_i| \times \theta\beta))$;

(7) the management device utilizes the additive homomorphic property of the cryptosystem to perform a calculation corresponding to $(|p_i \cap q|) \times (1+\theta\alpha+\theta\beta-\theta) + (-|q| \times \theta\alpha) + (-|p_i| \times \theta\beta)$ in plaintext on the encrypted value $Enc(|p_i \cap q|) \times (1+\theta\alpha+\theta\beta-\theta))$ determined in the above (5) and the encrypted value $Enc((-|q| \times \theta\alpha) + (-|p_i| \times \theta\beta))$ determined in the above (6), and determines an encrypted value $Enc(|p_i \cap q|) \times (1+\theta\alpha+\theta\beta-\theta) + (-|q| \times \theta\alpha) + (-|p_i| \times \theta\beta))$ as an encrypted value of a score $T_i$;

(8) the management device repeats the above (2) to (7) for each item of sequence data $p_i$ of a plurality of substances included in the database, and determines an encrypted value of the score $T_i$ for each of the items of sequence data $p_i$; and (9) the management device outputs encrypted values of the scores $T_1, T_2, \ldots, T_m$ to the searcher device.

* * * * *